United States Patent
Abraham et al.

(10) Patent No.: US 12,410,227 B2
(45) Date of Patent: Sep. 9, 2025

(54) INCRETIN ANALOGS AND USES THEREOF

(71) Applicant: Eli Lily and Company, Indianapolis, IN (US)

(72) Inventors: Milata Mary Abraham, Indianapolis, IN (US); Jorge Alsina-Fernandez, Indianapolis, IN (US); Tamer Coskun, Carmel, IN (US); Hongchang Qu, Carmel, IN (US); James Lincoln Wallis, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 723 days.

(21) Appl. No.: 17/785,758

(22) PCT Filed: Dec. 11, 2020

(86) PCT No.: PCT/US2020/064512
§ 371 (c)(1),
(2) Date: Jun. 15, 2022

(87) PCT Pub. No.: WO2021/126695
PCT Pub. Date: Jun. 24, 2021

(65) Prior Publication Data
US 2023/0102339 A1   Mar. 30, 2023

Related U.S. Application Data

(60) Provisional application No. 62/949,661, filed on Dec. 18, 2019.

(51) Int. Cl.
| | | |
|---|---|---|
| *C07K 14/575* | (2006.01) | |
| *A61P 3/04* | (2006.01) | |
| *A61P 3/06* | (2006.01) | |
| *A61P 3/10* | (2006.01) | |
| *A61K 38/00* | (2006.01) | |

(52) U.S. Cl.
CPC ............. *C07K 14/575* (2013.01); *A61P 3/04* (2018.01); *A61P 3/06* (2018.01); *A61P 3/10* (2018.01); *A61K 38/00* (2013.01)

(58) Field of Classification Search
CPC ....... C07K 14/575; C07K 14/605; A61P 3/04; A61P 3/10; A61K 38/00; A61K 38/26
See application file for complete search history.

(56) References Cited

U.S. PATENT DOCUMENTS

| | | | | |
|---|---|---|---|---|
| 8,507,428 B2* | 8/2013 | DiMarchi | ............. | A61P 3/10 |
| | | | | 514/5.3 |
| 8,551,946 B2* | 10/2013 | Dimarchi | ............. | A61K 38/26 |
| | | | | 514/21.3 |
| 10,131,702 B2* | 11/2018 | Just | ................. | A61P 29/00 |
| 2016/0310575 A1 | 10/2016 | Belli et al. | | |

FOREIGN PATENT DOCUMENTS

| | | |
|---|---|---|
| CA | 3084004 A1 | 6/2019 |
| CA | 3084005 A1 | 6/2019 |
| WO | 2016111971 A1 | 7/2016 |

OTHER PUBLICATIONS

Bastin, M., & Andreelli, F. (2019). Dual GIP-GLP1-receptor agonists in the treatment of type 2 diabetes: a short review on emerging data and therapeutic potential. *Diabetes, Metabolic Syndrome and Obesity: Targets and Therapy*, 12, 1973.

Mroz, P. A., Finan, B., Gelfanov, V., Yang, B., Tschöp, M. H., DiMarchi, R. D., & Perez-Tilve, D. (2019). Optimized GIP analogs promote body weight lowering in mice through GIPR agonism not antagonism. *Molecular metabolism*, 20, 51-62.

Patent Cooperation Treaty International Search Report pertaining to International Application No. PCT/US2020/064512; International Filing Date: Dec. 11, 2020; Date of Mailing: May 3, 2021.

Patent Cooperation Treaty Written Opinion of the International Searching Authority pertaining to International Application No. PCT/US2020/064512; International Filing Date: Dec. 11, 2020; Date of Mailing: May 3, 2021.

\* cited by examiner

*Primary Examiner* — Lianko G Garyu
*Assistant Examiner* — David Paul Bowles
(74) *Attorney, Agent, or Firm* — Matthew T. Lord

(57) ABSTRACT

Incretin analogs are provided that have activity at each of the glucose-dependent insulinotropic polypeptide (GIP), glucagon-like peptide-1 (GLP-1) and glucagon (GCG) receptors. The incretin analogs have structural features resulting in balanced activity and extended duration of action at each of these receptors. Methods also are provided for treating diseases such as type 2 diabetes mellitus, dyslipidemia, metabolic syndrome, non-alcoholic fatty liver disease, non-alcoholic steatohepatitis and obesity.

33 Claims, No Drawings
Specification includes a Sequence Listing.

INCRETIN ANALOGS AND USES THEREOF

The disclosure relates to incretin analogs having activity at each of a glucose-dependent insulinotropic polypeptide (GIP), glucagon-like peptide-1 (GLP-1) and glucagon (GCG) receptors. The incretin analogs herein have structural features that provide balanced activity at each of these receptors and that have an extended duration of action. Such incretin analogs may be useful for treating conditions, diseases and disorders including type 2 diabetes mellitus (T2DM), dyslipidemia, metabolic syndrome, non-alcoholic fatty liver disease (NAFLD), non-alcoholic steatohepatitis (NASH) and/or obesity, as well as cardiovascular diseases that are not considered metabolic diseases and neurodegenerative diseases.

Over the past several decades, the prevalence of diabetes continues to rise. T2DM is the most common form of diabetes accounting for about 90% of all diabetes. T2DM is characterized by high blood glucose levels stemming from insulin resistance. The current standard of care for T2DM includes diet and exercise, as well as treatment with oral medications and injectable glucose-lowering drugs including incretin-based therapies, such as GLP-1 receptor agonists.

GLP-1 is a 36-amino acid peptide, the major biologically active fragment of which is produced as a 30-amino acid, C-terminal amidated peptide (GLP-$1_{7-36}$; SEQ ID NO:2) that stimulates glucose-dependent insulin secretion and that prevents hyperglycemia in diabetics. A variety of GLP-1 analogs currently are available for treating T2DM, including dulaglutide, exenatide and liraglutide. Many currently marketed GLP-1 analogs, however, are dose-limited by gastrointestinal side effects, such as nausea and vomiting. When treatment with oral medications and incretin-based therapies is insufficient, treatment with insulin is considered. Despite the treatment options available, significant numbers of individuals receiving approved therapies are not reaching glycemic control goals (see, e.g., Casagrande et al. (2013) *Diabetes Care* 36:2271-2279).

Uncontrolled diabetes can lead to one or more conditions that impact morbidity and mortality of such individuals. One of the main risk factors for T2DM is obesity, and many individuals with T2DM (~90%) are overweight or obese. It is documented that a decrease in body adiposity will lead to improvement in obesity-associated co-morbidities including hyperglycemia and cardiovascular events. Therefore, therapies effective in glucose control and weight reduction are needed for better disease management.

In view thereof, new therapies being studied include compounds having not only activity at a GLP-1 receptor but also activity at one or more other receptors, such as the GIP and/or GCG receptors. In fact, certain compounds already have been described as having triple receptor agonist activity (i.e., activity at each of the GIP, GLP-1 and GCG receptors). For example, Intl. Patent Application Publication No. WO 2015/067716 describes GCG analogs having triple receptor agonist activity. Similarly, Intl. Patent Application Publication No. WO 2016/198624 describes exendin-4 analogs having triple receptor agonist activity. Likewise, Intl. Patent Application Publication Nos. WO 2014/049610 and WO 2017/116204 each describe a variety of compounds having triple receptor agonist activity. Moreover, Intl. Patent Application Publication No. WO 2017/153575 describes GCG and GLP-1 co-agonists that also are stated to have GIP receptor agonist activity.

Although typically used for treating T2DM, incretins and analogs thereof having activity at one or more of the GIP, GLP-1 and/or GCG receptors also have been described as having a potential for therapeutic value in a number of other conditions, diseases or disorders, including, for example, Alzheimer's disease, bone-related disorders, dyslipidemia, metabolic syndrome, NAFLD and NASH, obesity and Parkinson's disease. See, e.g., Jall et al. (2017) *Mol. Metab.* 6:440-446; Carbone et al. (2016) *J. Gastroenterol. Hepatol.* 31:23-31; Finan et al. (2016) *Trends Mol. Med.* 22:359-376; Choi et al. (2017) *Potent body weight loss and efficacy in a NASH animal model by a novel long-acting GLP-1/Glucagon/GIP triple-agonist (HM15211)*, ADA Poster 1139-P; Ding (2008) *J. Bone Miner. Res.* 23:536-543; Tai et al. (2018) *Brain Res.* 1678:64-74; Müller et al. (2017) *Physiol. Rev.* 97:721-766; Finan et al. (2013) *Sci. Transl. Med.* 5:209; Hölscher (2014) *Biochem. Soc. Trans.* 42:593-600.

Nevertheless, a need remains for treatments for such conditions, diseases and disorders, especially T2DM, that are capable of providing effective glucose control, with weight loss benefits and/or a favorable side effect profile. There also is a need for therapeutic agents available for use with sufficiently extended duration of action to allow for dosing as infrequently as once-a-day, thrice-weekly, twice-weekly or once a week.

The incretin analogs herein seek to meet the needs above. Accordingly, the disclosure describes incretin analogs with activity at each of the GIP, GLP-1 and GCG receptors. Advantageously, the incretin analogs herein have balanced activity at these receptors, thereby allowing for administration of doses that provide sufficient activity at each receptor to provide the benefits of agonism of that receptor while avoiding unwanted side effects associated with too much activity. Moreover, the incretin analogs herein have an extended duration of action at each of the GIP, GLP-1 and GCG receptors allowing for dosing as infrequently as once-a-day, thrice-weekly, twice-weekly or once-a-week. In this manner, the incretin analogs result in enhanced glucose control, metabolic benefits such as lowering body weight and/or improving body composition, lipid benefits such as lowering proprotein convertase subtilisin/kexin type 9 (PCSK9), and/or other benefits such as increasing bone mass or bone formation or decreasing bone resorption. The disclosure also describes effective treatments for conditions, diseases and disorders including T2DM, dyslipidemia, metabolic syndrome, NAFLD, NASH and/or obesity.

Accordingly, the disclosure first describes incretin analogs that include a base amino acid sequence of:

$YX_2QGTX_6TSDX_{10}SIX_{13}LDX_{16}X_{17}AQX_{20}X_{21}FIX_{24}X_{25}LLEGGPSSGEPP$ $PX_{39}$, where $X_2$ is Aib, $X_6$ is αMeF(2F), $X_{10}$ is Y or 4Pal, $X_{13}$ is L or αMeL, $X_{16}$ is O, $X_{17}$ is any amino acid with a functional group available for conjugation and the functional group is conjugated to a $C_{16}$-$C_{22}$ fatty acid moiety, $X_{20}$ is 4Pal, Iva or αMeL, $X_{21}$ is A or Aib, $X_{24}$ is E or e, $X_{25}$ is Y or αMeY, and $X_{39}$ is E or S (SEQ ID NO:5), and where a carboxy-terminal (C-terminal) amino acid optionally is amidated, or a pharmaceutically acceptable salt thereof.

In some instances, the amino acid with the functional group available for conjugation at position $X_{17}$ is C, D, E, K or Q. In certain instances, the amino acid with the functional group available for conjugation at position $X_{17}$ is K.

In certain instances, $X_2$ is Aib, $X_6$ is αMeF(2F), $X_{10}$ is Y, $X_{13}$ is L, $X_{16}$ is O, $X_{17}$ is K, $X_{20}$ is 4Pal, $X_{21}$ is A, $X_{24}$ is E, $X_{25}$ is Y and $X_{39}$ is E, such that the incretin analog includes a base amino acid sequence of:

(SEQ ID NO: 6)
Y-Aib-QGT-αMeF(2F)-TSDYSILLDOKAQ-4Pal-

AFIEYLLEGGPSSGEPPPE.

In certain instances, $X_2$ is Aib, $X_6$ is αMeF(2F), $X_{10}$ is Y, $X_{13}$ is αMeL, $X_{16}$ is O, $X_{17}$ is K, $X_{20}$ is Iva, $X_{21}$ is A, $X_{24}$ is E, $X_{25}$ is αMeY and $X_{39}$ is S, such that the incretin analog includes a base amino acid sequence of:

In some instances, the $C_{16}$-$C_{22}$ fatty acid moiety is conjugated to the amino acid with the functional group available for conjugation via a linker. In certain instances, the $C_{16}$-$C_{22}$ fatty acid moiety has a structure of —CO—$(CH_2)_a$—$CO_2H$, where a is an integer between 16 to 22. In certain instances, the fatty acid moiety is a $C_{18}$ diacid or a $C_{20}$. Likewise, and in some instances, the linker is one or more units of [2-(2-amino-ethoxy)-ethoxy)]-acetyl (AEEA), aminohexanoic acid (Ahx), E, γ-glutamic acid (γE) or combinations thereof.

In particular instances, the incretin analog herein, including the linker and the fatty acid moiety, can be one of the following:

(SEQ ID NO: 9)

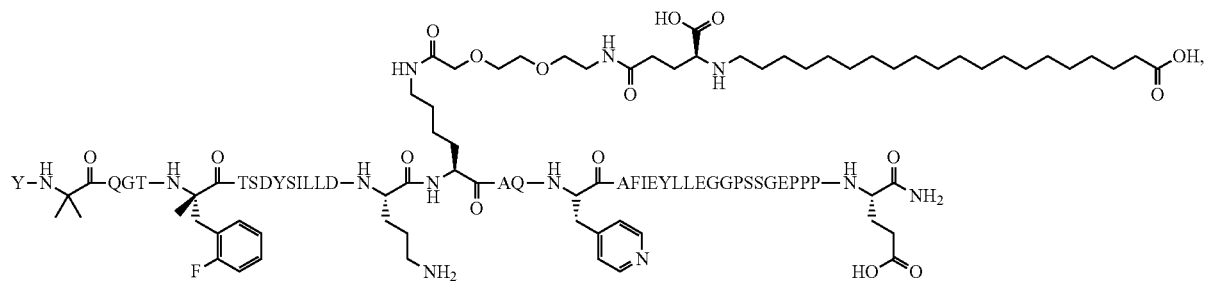

(SEQ ID NO: 10)

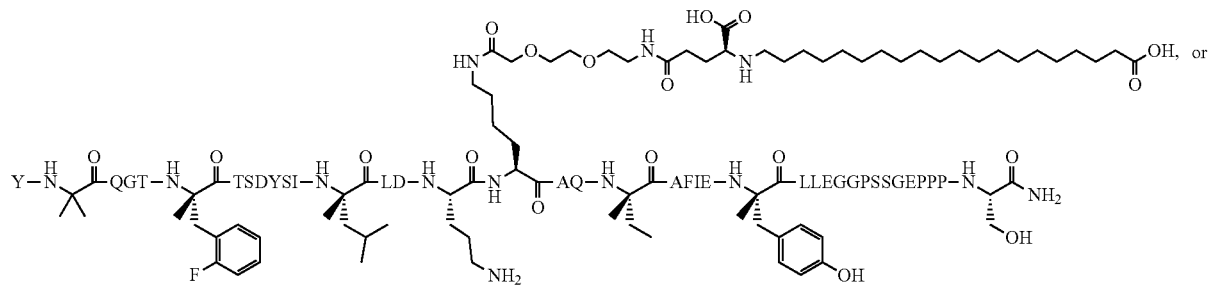

(SEQ ID NO: 11)

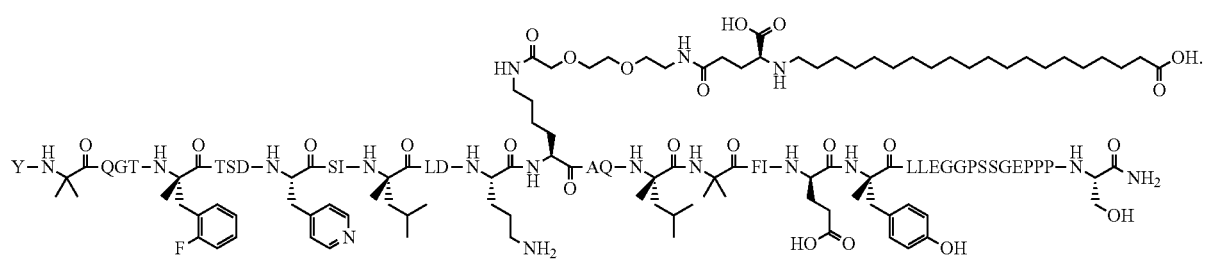

(SEQ ID NO: 7)
Y-Aib-QGT-αMeF(2F)-TSDYSI-αMeL-LDOKAQ-Iva-AFIE-

αMeY-LLEGGPSSGEPPPS.

In certain instances, $X_2$ is Aib, $X_6$ is αMeF(2F), $X_{10}$ is 4Pal, $X_{13}$ is αMeL, $X_{16}$ is O, $X_{17}$ is K, $X_{20}$ is αMeL, $X_{21}$ is Aib, $X_{24}$ is e, $X_{25}$ is αMeY and $X_{39}$ is S, such that the incretin analog includes a base amino acid sequence of:

(SEQ ID NO: 8)
Y-Aib-QGT-αMeF(2F)-TSD-4Pal-SI-αMeL-LDOKAQ-αMeL-

Aib-FIe-αMeY-LLEGGPSSGEPPPS.

Second, pharmaceutical compositions are described that include at least one incretin analog herein or a pharmaceutically acceptable salt thereof (e.g., trifluroacetate salts, acetate salts or hydrochloride salts) and a pharmaceutically acceptable carrier. In some instances, the pharmaceutical compositions further can include carriers, diluents and/or excipients.

Third, methods are described for treating a disease such as T2DM, dyslipidemia, metabolic syndrome, NAFLD, NASH and obesity. Such methods can include at least a step of administering to an individual in need thereof an effective amount of an incretin analog described herein. In some instances, the disease is T2DM, NAFLD, NASH or obesity. In other instances, the disease is a cardiovascular disease that is not considered a metabolic disease or a neurodegenerative disease.

In some instances, the at least one incretin analog herein can be subcutaneously (SQ) administered to the individual. Likewise, and in some instances, the at least one incretin analog can be administered daily, every other day, three times a week, two times a week, one time a week (i.e., weekly), biweekly (i.e., every other week) or monthly. In certain instances, the at least one incretin analog can be administered SQ every other day, SQ three times a week, SQ two times a week, SQ one time a week, SQ every other week, or SQ once a month. In particular instances, the at least one incretin analog is administered SQ one time a week (QW).

The methods also may include steps such as measuring or obtaining the individual's weight or body composition and/or blood glucose and/or blood insulin and/or hemoglobin A1c (HbA1c) and/or blood lipid, and then comparing such obtained values to one or more baseline values or previously obtained values to assess the effectiveness of treatment.

In some instances, the individual is obese or overweight. In other instances, the individual is a person with diabetes (PwD), especially T2DM. In certain instances, the individual is obese with T2DM or overweight with T2DM.

The methods also may be combined with diet and exercise and/or may be combined with additional therapeutic agents.

Fourth, incretin analogs are described for use in therapy, such as for use in treating a disease such as T2DM, dyslipidemia, metabolic syndrome, NAFLD, NASH and obesity. In some instances, the disease is T2DM, NAFLD, NASH or obesity. In other instances, the disease is a cardiovascular disease that is not considered a metabolic disease or a neurodegenerative disease.

Fifth, uses are described for the incretin analogs herein in manufacturing a medicament for treating T2DM, dyslipidemia, metabolic syndrome, NAFLD, NASH and obesity. In some instances, the disease is T2DM, NAFLD, NASH or obesity. In other instances, the disease is a cardiovascular disease that is not considered a metabolic disease or a neurodegenerative disease.

Unless defined otherwise, all technical and scientific terms used herein have the same meaning as commonly understood by one of skill in the art to which the disclosure pertains. Although any methods and materials similar to or equivalent to those described herein can be used in the practice or testing of the incretin analogs, pharmaceutical compositions and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Definitions

As used herein, "about" means within a statistically meaningful range of a value or values such as, for example, a stated concentration, length, molecular weight, pH, sequence identity, time frame, temperature or volume. Such a value or range can be within an order of magnitude typically within 20%, more typically within 10%, and even more typically within 5% of a given value or range. The allowable variation encompassed by "about" will depend upon the particular system under study, and can be readily appreciated by one of skill in the art.

As used herein, and in reference to one or more of the GIP, GLP-1 or GCG receptors, "activity," "activate," "activating" and the like means a capacity of a compound, such as the incretin analogs herein, to bind to and induce a response at the receptor(s), as measured using assays known in the art, such as the in vitro assays described below.

As used herein, "amino acid" means a molecule that, from a chemical standpoint, is characterized by containing one or more amine groups and one or more carboxylic acid groups, and may contain other functional groups. As is known in the art, there is a set of twenty amino acids that are designated as standard amino acids and that are used as building blocks for most of the peptides/polypeptides/proteins produced by any living being.

As used herein, "amino acid with a functional group available for conjugation" means any standard or non-standard amino acid with a functional group that may be conjugated to a fatty acid moiety by way of, for example, a linker. Examples of such functional groups include, but are not limited to, alkynyl, alkenyl, amino, azido, bromo, carboxyl, chloro, iodo and thiol groups. Additionally, examples of standard amino acids including such functional groups include C (thiol), D (carboxyl), E (carboxyl), K (amino) and Q (amide).

As used herein, "analog" means a compound, such as a synthetic peptide or polypeptide, that activates a target receptor and that elicits at least one in vivo or in vitro effect elicited by a native receptor agonist.

As used herein, "cardiovascular disease that is not considered a metabolic disease" and the like means a disease such as, for example, atherosclerosis or heart failure.

As used herein, "$C_{16}$-$C_{22}$ fatty acid" means a carboxylic acid having between 16 and 22 carbon atoms. The $C_{16}$-$C_{22}$ fatty acid suitable for use herein can be a saturated monoacid or a saturated diacid ("diacids" have a carboxyl group on each end).

As used herein, "effective amount" means an amount, concentration or dose of one or more of the incretin analogs herein, or a pharmaceutically acceptable salt thereof which, upon single or multiple dose administration to an individual in need thereof, provides a desired effect in such an individual under diagnosis or treatment (i.e., may produce a clinically measurable difference in a condition of the individual such as, for example, a reduction in blood glucose, a reduction in HbA1c, a reduction in weight or body fat and/or a change body composition). An effective amount can be readily determined by one of skill in the art by using known techniques and by observing results obtained under analogous circumstances. In determining the effective amount for an individual, a number of factors are considered, including, but not limited to, the species of mammal, its size, age and general health, the specific disease or disorder involved, the degree of or involvement or the severity of the disease or disorder, the response of the individual, the particular incretin analog administered, the mode of administration, the bioavailability characteristics of the preparation administered, the dose regimen selected, the use of concomitant medication, and other relevant circumstances.

As used herein, "extended duration of action" means that binding affinity and activity of an incretin analog continues for a period of time greater than native human GIP, GLP-1 and GCG, allowing for dosing at least as infrequently as once daily or even thrice-weekly, twice-weekly or once-weekly. The time action profile of the incretin analog may be measured using known pharmacokinetic test methods such as those utilized in the examples below.

As used herein, "glucose-dependent insulinotropic polypeptide" or "GIP" means a 42-amino acid peptide (SEQ ID NO:1) that is an incretin, which plays a physiological role in glucose homeostasis by stimulating insulin secretion from pancreatic beta cells in the presence of glucose.

As used herein, "glucagon-like peptide-1" or "GLP-1" means a 36-amino acid peptide (SEQ ID NO:2) that also is an incretin, which stimulates glucose-dependent insulin secretion and which has been shown to prevent hyperglycemia in diabetics.

As used herein, "glucagon" or "GCG" means a 29-amino acid peptide (SEQ ID NO:3) that helps maintain blood glucose by binding to and activating GCG receptors on hepatocytes, causing the liver to release glucose—stored in the form of glycogen—through a process called glycogenolysis.

As used herein, "oxyntomodulin" or "OXM" means a 37-amino acid peptide (SEQ ID NO:4) that includes not only the 29-amino acid sequence of GCG but also an octapeptide carboxy terminal extension that activates both the GCG and GLP-1 receptors, with a slightly higher potency for the GCG receptor over the GLP-1 receptor.

As used herein, "half-maximal effective concentration" or "$EC_{50}$" means a concentration of compound that results in 50% activation/stimulation of an assay endpoint, such as a dose-response curve (e.g., cAMP).

As used herein, "incretin analog" means a compound having structural similarities with, but multiple differences from, each of GIP, GLP-1 and GCG, especially human GIP (SEQ ID NO:1), human GLP-1 (SEQ ID NO:2) and human GCG (SEQ ID NO:3). The incretin analogs herein include amino acid sequences resulting in the compounds having affinity for and activity at each of the GIP, GLP-1 and GCG receptors (i.e., triple receptor agonist activity).

As used herein, "individual in need thereof" means a mammal, such as a human, with a condition, disease, disorder or symptom requiring treatment or therapy, including for example, those listed herein. In particular, the preferred individual to be treated is a human.

As used herein, "long-acting" means that binding affinity and activity of an incretin analog herein continues for a period of time greater than a reference peptide such as native, human GIP (SEQ ID NO:1), human GLP-1 (SEQ ID NO:2) and/or human GCG (SEQ ID NO:3), allowing for dosing at least as infrequently as once-daily, thrice-weekly, twice-weekly, once-weekly or even monthly. The time action profile of the incretin analogs herein may be measured using known pharmacokinetic methods such as those described in the Examples below.

As used herein, "non-standard amino acid" means an amino acid that may occur naturally in cells but does not participate in peptide synthesis. Non-standard amino acids can be constituents of a peptide and can be generated by modifying standard amino acids in the peptide (i.e., via post-translational modification). Non-standard amino acids can include D-amino acids, which have an opposite absolute chirality of the standard, L-amino acids above.

As used herein, "saturated" means that a fatty acid moiety that contains no carbon-carbon double or triple bonds.

As used herein, "treat," "treating," "to treat" and the like mean restraining, slowing, stopping or reversing the progression or severity of an existing condition, disease, disorder or symptom.

As used herein, and with reference to an incretin analog, "triple receptor agonist activity" means an incretin analog with activity at each of the GIP, GLP-1 and GCG receptors, especially an analog having a balanced and sufficient activity at each receptor to provide the benefits of agonism of that receptor while avoiding unwanted side effects associated with too much activity of that receptor. Moreover, the incretin analogs having triple receptor agonist activity have extended duration of action at each of the GIP, GLP-1 and GCG receptors, which advantageously allows for dosing as infrequently as once-a-day, thrice-weekly, twice-weekly or once-a-week.

Certain abbreviations are defined as follows: "4Pal" refers to 3-(4-pyridyl)-L-alanine; "ACR" refers to urine albumin/urine creatinine ratio; "Aib" refers to α-aminoisobutyric acid; "αMeL" refers to α-methyl leucine; "αMeK" refers to α-methyl lysine; "αMeF" refers to α-methyl phenylalanine; "αMeF(2F)" refers to α-methyl 2-fluoropheynylalanine; "αMeY" refers to α-methyl tyrosine; "amu" refers to atomic mass unit; "AUC" refers to area under the curve; "Boc" refers to tert-butoxycarbonyl; "cAMP" refers to cyclic adenosine monophosphate; "DMSO" refers to dimethyl sulfoxide; "EIA/RIA" refers to enzyme immunoassay/radioimmunoassay; "Fmoc" refers to fluorenylmethyloxycarbonyl; "hr" refers to hour or hours; "HTRF" refers to homogenous time-resolved fluorescent; "IV" refers to intravenous; "Iva" refers to isovaline; "kDa" refers to kilodaltons; "LC-MS" refers to liquid chromatography-mass spectrometry; "min" refers to minute or minutes; "MS" refers to mass spectrometry; "Orn" or "O" refers to ornithine; "OtBu" refers to O-tert-butyl; "Pbf" refers to NG-2,2,4,6,7-pentamethyldihydrobenzofuran-5-sulfonyl; "RP-HPLC" refers to reversed-phase high performance liquid chromatography; "sec" refers to second or seconds; "SEM" refers to standard error of the mean; "SPA" refers to scintillation proximity assay; "SQ" refers to subcutaneous; "TFA" refers to trifluoroacetic acid; "tBu" refers to tert-butyl; and "Trt" refers to Trityl.

Incretin Analogs

The structural features of the incretin analogs herein result in compounds having sufficient activity at each of the GIP, GLP-1 and GCG receptors to obtain the favorable effects of activity at each receptor (i.e., triple receptor agonist activity), but not so much activity at any one receptor to either overwhelm the activity at either of the other two receptors or result in undesirable side effects when administered at a dose sufficient to result in activity at all three receptors. Non-limiting examples of such structural features in certain embodiments, and with reference to SEQ ID NO:5, include αMeF(2F) at position 6, which contributes to optimal GCG, GIP and GLP-1 activity; Y or 4Pal at position 10, which contributes to balanced activity; L or αMeL at position 13, which contributes to optimal GCG and GIP activity; O at position 16, which contributes to balanced activity; acylation at position 17, which contributes to balanced activity; 4Pal, Iva or αMeL at position 20, which contributes to optimal GCG activity; A or Aib at position 21, which contributes to optimal GCG activity; Y or αMeY at position 25, which contributes to balanced activity. Other examples of such structural features include the amino acids described herein at positions 28-39, which contribute to optimal binding and potency at all three receptors.

The structural features of the incretin analogs herein also result in analogs having many other beneficial attributes relevant to their developability as therapeutic treatments, including improving the solubility of the analogs in aqueous solutions, improving chemical and physical formulation stability, extending the pharmacokinetic profile, and minimizing potential for immunogenicity. Non-limiting examples of particular structural features that result in such attributes include acylation at position 17 with a $C_{20}$ fatty acid, which contributes to optimal pharmacokinetic (PK) profiles and developability; 4Pal at position 10 or 20, which contributes to optimal solubility and chemical stability; O at position 16, which contributes to optimal solubility and PK; E or e at position 24, which contributes to optimal solubility and stability; Y or αMeY at position 25, which contributes to optimal chemical stability; and E or S at position 39, which contributes to optimal solubility; and the amino acids described herein at positions 6, 13, 16 and 28-39, which contribute to optimal PK, immunogenicity, developability and stability.

It should be noted that the foregoing lists of structural features are exemplary, and not comprehensive, and that the combination of beneficial characteristics of exemplary analogs described herein is not the result of any modification in isolation, but is instead achieved through the novel combinations of the structural features described herein. In addition, the above-described effects of the foregoing lists of modifications are not exclusive, as many of these modifications also have other effects important to the characteristics of the compounds described herein, as described below.

The amino acid sequences of incretin analogs herein incorporate naturally occurring (standard) amino acids, typically depicted herein using one letter codes (e.g., L=leucine; K=lysine), as well as non-standard and/or α-methyl substituted residues of standard amino acids (e.g., αMeL, αMeK, αMeF, αMeF(2F) and αMeY, and certain other non-standard amino acids, such as 4Pal, Aib, Iva, O and D-glutamic acid (e)). For clarity, the structures of these other amino acids are depicted below:

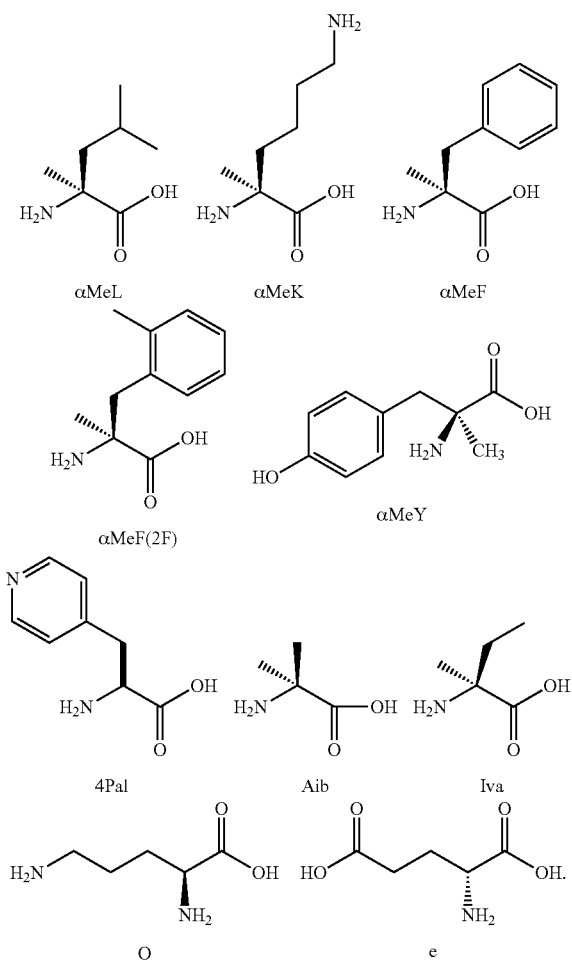

As noted above, the incretin analogs herein have structural similarities to, but many structural differences, from any of the native human peptides. For example, when compared to native human GIP (SEQ ID NO:1), the incretin analogs include modifications at one or more of positions 2-3, 6-7, 13-14, 16-18, 20-21, 23-25 and 28-42. In some instances, the incretin analogs include modifications to the amino acids of native human GIP (SEQ ID NO:1) at each of positions 2-3, 6-7, 13-14, 16-18, 20-21, 23-25 and 28-42. In certain instances, the incretin analogs include the following amino acid modifications: Aib at position 2; Q at position 3; αMeF(2F) at position 6; T at position 7; Y or 4Pal at position 10; L or αMeL at position 13; L at position 14; a modified K residue at position 17, which is modified through conjugation to the epsilon-amino group of the K-side chain with a $C_{16}$ to $C_{22}$ fatty acid, optionally through the use of a linker; A at position 18; 4Pal, Iva or αMeL at position 20; A or Aib at position 21; I at position 23; E or e at position 24; Y or αMeY at position 25; E at position 28; G at position 29; and replacement of the amino acids at positions 30-42 with the following amino acid sequence: GPSSGAPPPE (SEQ ID NO:12) or GPSSGAPPPS (SEQ ID NO:13) (and truncated analogs of either of these tails). In yet other instances, the incretin analogs are amidated. In addition to the modifications described herein, the incretin analogs may include one or more additional amino acid modifications such as an addition, deletion, insertion and/or substitution, but remain capable of binding to and activating each of the GIP, GLP-1 and GCG receptors.

As noted above, the incretin analogs herein include a fatty acid moiety conjugated, for example, by way of a linker to a standard or non-standard amino acid with a functional group available for conjugation. Such a conjugation is sometimes referred to as acylation. In certain instances, the amino acid with a functional group available for conjugation can be C, D, E, K or Q. In particular instances, the amino acid with a functional group available for conjugation is K, where the conjugation is to the epsilon-amino group of the K side-chain.

The acylation of the incretin analogs herein is at position 17 in SEQ ID NO:5, which is determined to be an optimal location for including this structure. The fatty acid moiety, and in certain instances the linker, acts as an albumin binder and provides a potential to generate long-acting compounds.

The incretin analogs herein utilize a $C_{16}$-$C_{22}$ fatty acid moiety chemically conjugated to the functional group of an amino acid either by a direct bond or by a linker. The length and composition of the fatty acid moiety impacts the half-life of the incretin analogs, the potency of the incretin analogs in in vivo animal models, and the solubility and stability of the incretin analogs. Conjugation to a $C_{16}$-$C_{22}$ saturated fatty monoacid or diacid results in incretin analogs that exhibit desirable half-life, desirable potency in in vivo animal models, and desirable solubility and stability characteristics.

Examples of saturated $C_{16}$-$C_{22}$ fatty acids for use herein include, but are not limited to, palmitic acid (hexadecanoic acid) ($C_{16}$ monoacid), hexadecanedioic acid ($C_{16}$ diacid), margaric acid (heptadecanoic acid)($C_{17}$ monoacid), heptadecanedioic acid ($C_{17}$ diacid), stearic acid ($C_{18}$ monoacid), octadecanedioic acid ($C_{18}$ diacid), nonadecylic acid (nonadecanoic acid)($C_{19}$ monoacid), nonadecanedioic acid ($C_{19}$ diacid), arachadic acid (eicosanoic acid)($C_{20}$ monoacid), eicosanedioic acid ($C_{20}$ diacid), heneicosylic acid (heneicosanoic acid)($C_{21}$ monoacid), heneicosanedioic acid ($C_{21}$ diacid), behenic acid (docosanoic acid)($C_{22}$ monoacid), docosanedioic acid ($C_{22}$ diacid), including branched and substituted derivatives thereof.

In certain instances, the $C_{16}$-$C_{22}$ fatty acid can be a saturated $C_{20}$ monoacid, a saturated $C_{20}$ diacid, and branched and substituted derivatives thereof. In more particular instances, the $C_{16}$-$C_{22}$ fatty acid can be eicosanedioic acid.

In some instances, the linker can have from one to four amino acids, an amino polyethylene glycol carboxylate or mixtures thereof. In certain instances, the amino polyethylene glycol carboxylate has the following structure:

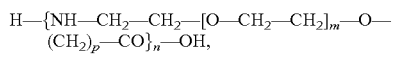

where m is any integer from 1 to 12, n is any integer from 1 to 12, and p is 1 or 2.

In certain instances, the linker can have one or more AEEA moieties, optionally in combination with one to four amino acids.

In instances in which the linker includes at least one amino acid, the amino acid can be one to four E or γE amino acid residues. In some instances, the linker can include one or two E or γE amino acid residues, including the D-forms thereof. For example, the linker can include either one or two γE amino acid residues. Alternatively, the linker can include one to four amino acid residues (such as, for example, E or γE amino acids) used in combination with up to thirty-six AEEA moieties. Specifically, the linker can be combinations of one to four E or γE amino acids and one to four AEEA moieties. In other instances, the linker can be combinations of one or two γE amino acids and one or two AEEA moieties.

In a specific instance, the incretin analogs herein have a linker-fatty acid moiety having the following structure:

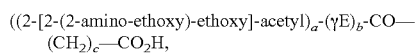

where a is 0, 1 or 2, b is 1 or 2, and c is 16 or 18. In a particular instance, a is 1, b is 1 and c is 20, having the following structure:

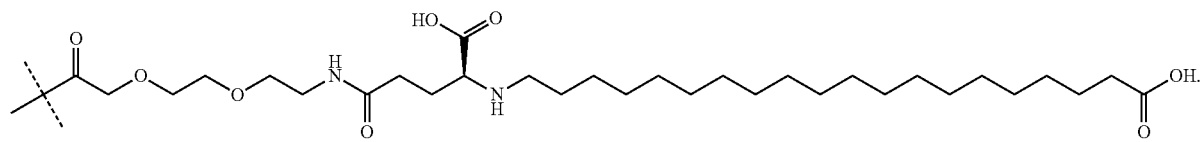

As shown in the chemical structures of Examples 1-3 below, the linker-fatty acid moiety described above can be linked to the epsilon (ε)-amino group of the K side-chain.

The affinity of the incretin analogs herein for each of the GIP, GLP-1 and GCG receptors may be measured using techniques known in the art for measuring receptor binding levels, including, for example, those described in the examples below, and is commonly expressed as an inhibitory constant (Ki) value. The activity of the incretin analogs at each of the receptors also may be measured using techniques known in the art, including, for example, the in vitro activity assays described below, and is commonly expressed as an effective concentration 50 ($EC_{50}$) value, which is the concentration of compound causing half-maximal simulation in a dose response curve.

The incretin analogs herein can be formulated as pharmaceutical compositions, which can be administered by parenteral routes (e.g., subcutaneous, intravenous, intraperitoneal, intramuscular or transdermal). Such pharmaceutical compositions and techniques for preparing the same are well known in the art. See, e.g., Remington: The Science and Practice of Pharmacy (Troy, Ed., 21$^{st}$ Edition, Lippincott, Williams & Wilkins, 2006). In particular instances, the incretin analogs are administered subcutaneous.

The incretin analogs herein may react with any of several inorganic and organic acids/bases to form pharmaceutically acceptable acid/base addition salts. Pharmaceutically acceptable salts and common techniques for preparing them are well known in the art (see, e.g., Stahl, et al. Handbook of Pharmaceutical Salts: Properties, Selection and Use, 2$^{nd}$ Revised Edition (Wiley-VCH, 2011)). Pharmaceutically acceptable salts for use herein include, but are not limited to, sodium, trifluoroacetate, hydrochloride, and acetate salts.

The disclosure also provides and therefore encompasses novel intermediates and methods of synthesizing the incretin analogs herein, or a pharmaceutically acceptable salt thereof. The intermediates and incretin analogs herein can be prepared by a variety of techniques known in the art. For example, a method using chemical synthesis is illustrated in the Examples below. The specific synthetic steps for each of the routes described may be combined in different ways to prepare incretin analogs herein. The reagents and starting materials are readily available to one of skill in the art.

Certain incretin analogs herein are generally effective over a wide dosage range. For example, dosages for once-weekly administration may fall within a range of about 0.01 to about 30 mg/individual/week, within a range of about 0.1 to about 10 mg/individual/week, or even within a range of about 0.1 to about 3 mg/individual/week. Thus, the incretin analogs herein may be dosed daily, thrice-weekly, twice-weekly or once-weekly, especially once-weekly administration.

The incretin analogs herein may be used for treating a variety of conditions, disorders, diseases or symptoms. In particular, methods are provided for treating T2DM in an individual, where such methods include at least a step of administering to an individual in need of such treatment an effective amount of an incretin analog herein, or a pharmaceutically acceptable salt thereof.

Additionally, methods are provided for treating dyslipidemia in an individual, where such methods include at least a step of administering to an individual in need of such treatment an effective amount of an incretin analog herein, or a pharmaceutically acceptable salt thereof.

Additionally, methods are provided for treating metabolic syndrome in an individual, where such methods include at least a step of administering to an individual in need of such treatment an effective amount of an incretin analog herein, or a pharmaceutically acceptable salt thereof.

Additionally, methods are provided for treating NAFLD in an individual, where such methods include at least a step of administering to a subject in need of such treatment an effective amount of an incretin analog herein, or a pharmaceutically acceptable salt thereof.

Additionally, methods are provided for treating NASH in an individual, where such methods include at least a step of administering to an individual in need of such treatment an effective amount of an incretin analog herein, or a pharmaceutically acceptable salt thereof.

Additionally, methods are provided for treating obesity in an individual, where such methods include at least a step of administering to an individual in need of such treatment an effective amount of an incretin analog herein, or a pharmaceutically acceptable salt thereof.

Additionally, methods are provided for inducing non-therapeutic weight loss in an individual, where such methods include at least a step of administering to an individual in need of such treatment an effective amount of an incretin analog herein, or a pharmaceutically acceptable salt thereof.

Additionally, methods are provided for treating a cardio-vascular disease that is not considered a metabolic disease, where such methods include at least a step of administering to an individual in need of such treatment an effective amount of an incretin analog herein, or a pharmaceutically acceptable salt thereof.

Additionally, methods are provided for treating a neurodegenerative disease, where such methods include at least a step of administering to an individual in need of such treatment an effective amount of an incretin analog herein, or a pharmaceutically acceptable salt thereof.

In these methods, effectiveness of the incretin analogs herein can be assessed by, for example, observing a significant reduction in blood glucose, observing a significant increase in insulin, observing a significant reduction in HbA1c, observing a significant decrease in a blood lipid, observing a significant reduction in weigh or body fat and/or observing a change in body composition.

Alternatively, the incretin analogs herein or pharmaceutically acceptable salts thereof may be used for improving bone strength in an individual in need thereof. In some instances, the individual in need thereof has hypoostosis or hypoosteoidosis, or is healing from bone fracture, orthotic procedure, prosthetics implant, dental implant and/or spinal fusion. The incretin analogs also may be used for treating other disorders such as Alzheimer's disease or Parkinson's disease.

EXAMPLES

The following non-limiting examples are offered for purposes of illustration, not limitation.
Polypeptide Synthesis Example 1: Synthesis of Incretin Analog 1

Example 1 is a compound represented by the following description:

```
                                              (SEQ ID NO: 9)
YAibQGT-αMeF(2F)-TSDYSILLDOK(2-[2-(2-aminoethoxy)-ethoxy]-acetyl-γE-CO—(CH₂)₁₈—CO₂H)AQ- 4Pal-AFIEYLLEGGPSSGEPPPE-NH₂.
```

Below is a depiction of the structure of Example 1 using the standard single letter amino acid codes except for residues Aib2, αMeF(2F)6, O16, K17, 4Pal20 and E39 where the structures of these amino acid residues have been expanded:

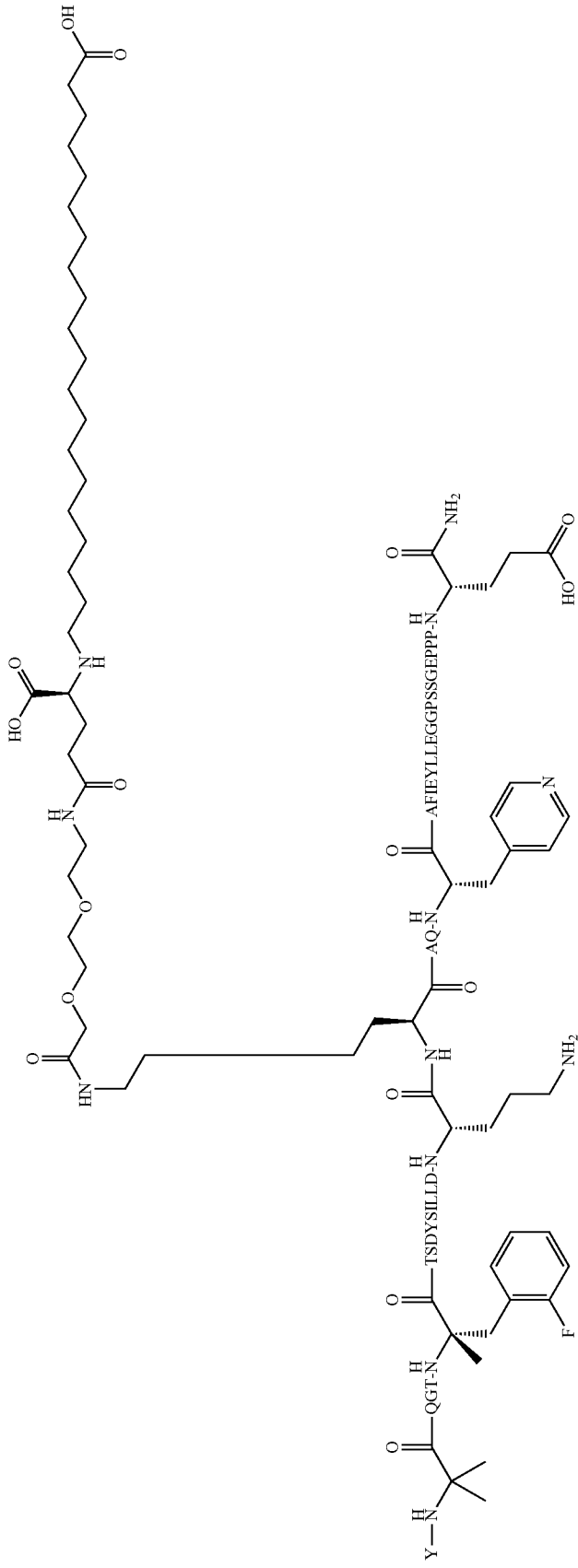

The peptide backbone of Example 1 is synthesized using Fmoc/t-Bu chemistry on a Symphony X peptide synthesizer (Gyros Protein Technologies; Tucson, AZ).

The resin is 1% DVB cross-linked polystyrene (Fmoc-Rink-MBHA low-loading resin, 100-200 mesh; EMD Millipore) at a substitution of 0.3-0.4 meq/g. Standard side-chain protecting groups are used with the following exceptions. Fmoc-Lys(Mtt)-OH is used for the K at position 17, and Boc-Tyr(tBu)-OH is used for the Y at position 1. Fmoc groups are removed prior to each coupling step (2×7 min) using 20% piperidine in DMF. All standard amino acid couplings are performed for 1 hr to a primary amine and for 3 hr to a secondary amine using an equal molar ratio of Fmoc amino acid (0.3 mM), diisopropylcarbodiimide (0.9 mM) and Oxyma (0.9 mM), at a nine-fold molar excess over the theoretical peptide loading. Exceptions are couplings to Cα-methylated amino acids, which are coupled for 3 hr. After completing synthesis of the peptide backbone, the resin is thoroughly washed with DCM for six times to remove residual DMF. The Mtt protecting group on the K at position 17 is selectively removed from the peptide resin using two treatments of 30% hexafluoroisopropanol (Oakwood Chemicals) in DCM (2×40-minute treatment).

Subsequent attachment of the fatty acid-linker moiety is accomplished by coupling 2-[2-(2-Fmoc-amino-ethoxy)-ethoxy]-acetic acid (Fmoc-AEEA-OH, ChemPep, Inc.), Fmoc-glutamic acid α-t-butyl ester (Fmoc-E-OtBu, Ark Pharm, Inc.) and mono-OtBu-eicosanoic acid (WuXi AppTec, Shanghai, China). A three-fold excess of reagents (AA:PyAOP:DIPEA=1:1:1 mol/mol) is used for each coupling for 1 hr.

After synthesis is complete, the peptide resin is washed with DCM and then thoroughly air-dried. The dry resin is treated with 10 mL of a cleavage cocktail (TFA:triisopropylsilane:water, 92.5:2.5:5 by volume) for 30 min at 40° C. The resin is filtered off, washed twice each with 2 mL of neat TFA, and the combined filtrates are treated with five-fold excess volume of cold diethyl ether (−20° C.) to precipitate the crude peptide. The peptide/ether suspension is then centrifuged at 3500 rpm for 2 min to form a solid pellet, the supernatant is decanted, and the solid pellet is triturated with cold ether two additional times and dried in vacuo. The crude peptide is solubilized in 20% acetonitrile/20% acetic acid/60% water and purified by RP-HPLC on a Luna 5 μm Phenyl-Hexyl preparative column (21×250 mm; Phenomenex) with linear gradients of 100% acetonitrile and 0.1% TFA/water buffer system (30-50% acetonitrile in 60 min). The purity of peptide is assessed using analytical RP-HPLC and pooling criteria is >95%. The main pool purity of Example 1 is found to be >98.0%. Subsequent lyophilization of the final main product pool yields the lyophilized peptide TFA salt. The molecular weight is determined by LC-MS (obsd: M+3=1633.7; Calc M+3=1633.8).

Example 2: Synthesis of Incretin Analog 2

Example 2 is a compound represented by the following description:

```
                                            (SEQ ID NO: 10)
YAibQGT-αMeF(2F)-TSDYSI-αMeL-LDOK(2-[2-(2-aminoethoxy)-ethoxy]-acetyl-γE-CO-(CH2)18-CO2H)AQ- Iva-AFIE-αMeY-LLEGGPSSGEPPPS-NH2.
```

Below is a depiction of the structure of Example 2 using the standard single letter amino acid codes except for residues Aib2, αMeF(2F)6, αMeL13, O16, K17, Iva20, αMeY25 and S39 where the structures of these amino acid residues have been expanded:

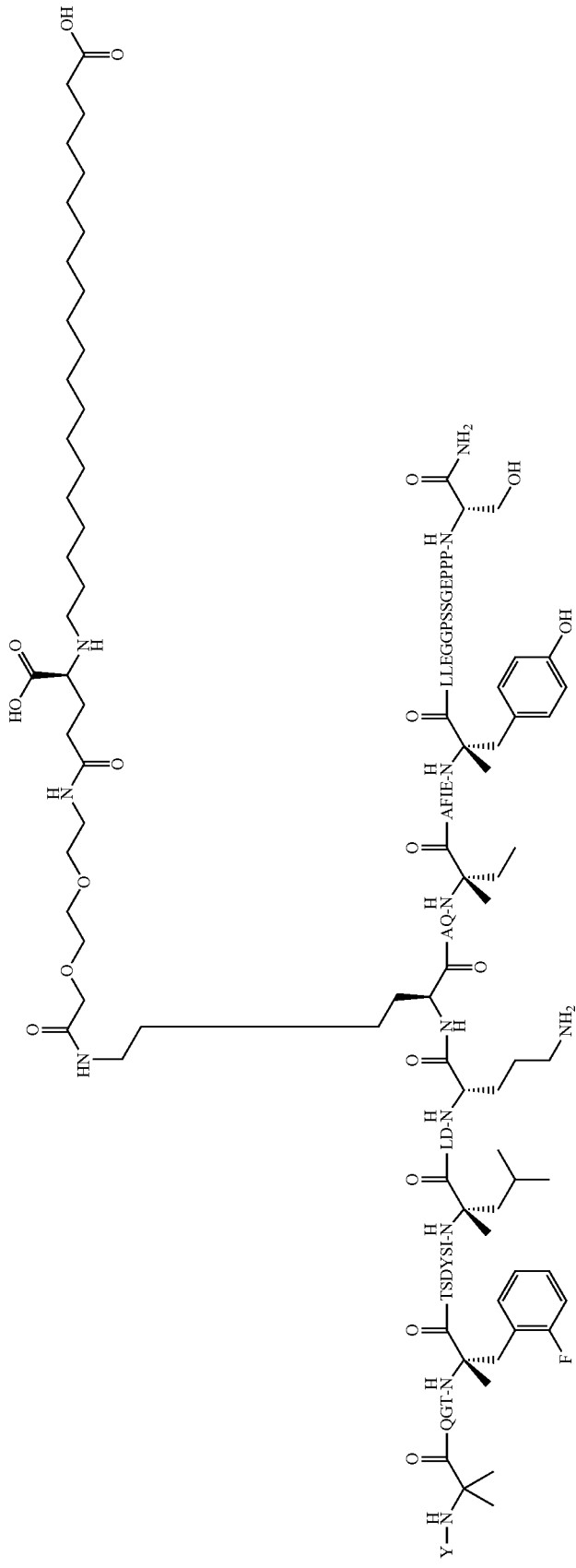

Similar processes to those described above for Example 1 are used to synthesize the peptide backbone, to conjugate the fatty acid-linker moiety, to examine the purity, and to confirm the molecular weight of Example 2.

Example 3: Synthesis of Incretin Analog 3

Example 3 is a compound represented by the following description:

(SEQ ID NO: 11)
YAibQGT-αMeF(2F)-TSD-4Pal-SI-αMeL-LDOK(2-[2-(2-amino-ethoxy)-ethoxy]-acetyl-γE-CO—(CH$_2$)$_{18}$—CO$_2$H)AQ-αMeL-Aib-FIe-αMeY-LLEGGPSSGEPPPS-NH$_2$.

Below is a depiction of the structure of Example 3 using the standard single letter amino acid codes except for residues Aib2, αMeF(2F)6, 4Pal10, αMeL13, O16, K17, αMeL20, Aib21, e24, αMeY25 and S39 where the structures of these amino acid residues have been expanded:

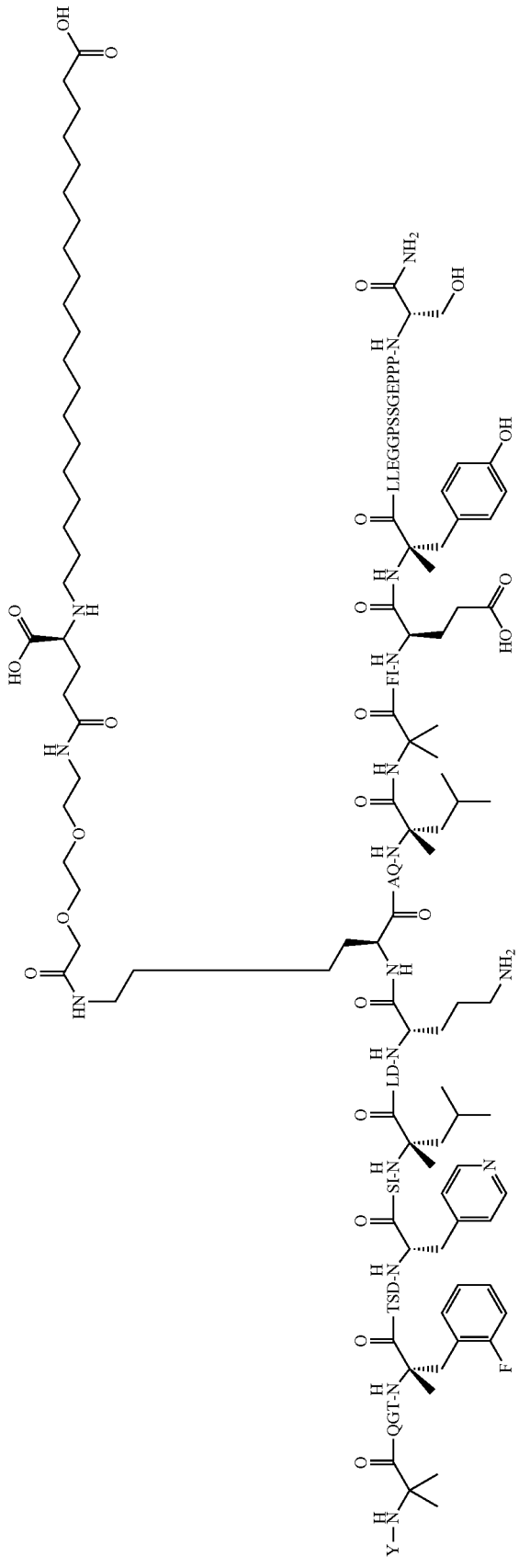

Similar processes to those described above for Example 1 are used to synthesize the peptide backbone, to conjugate the fatty acid-linker moiety, to examine the purity, and to confirm the molecular weight of Example 3.

In Vitro Function

Example 4: Binding Affinity

Radioligand competition binding assays are used to determine the equilibrium dissociation constant for the Example compounds and comparators. Such assays use SPA methods and membranes prepared from transfected HEK293 cells overexpressing human GIP receptor (hGIPR; SEQ ID NO:14), human GLP-1 receptor (hGLP-1R; SEQ ID NO:15) or human GCG receptor (hGCGR; SEQ ID NO:16).

The assays are performed in the presence of bacitracin as a non-specific blocking agent to prevent acylated moieties of test analogs from binding to protein components used in standard assay buffers (e.g., albumin).

Competition curves are plotted as the percent specific inhibition (y-axis) versus log concentration of compound (x-axis) and analyzed using a four-parameter nonlinear regression fit with variable slope (ABase or Genedata). $K_i$ values are calculated according to the equation $K_i=IC_{50}/(1+(D/K_d))$, where $IC_{50}$ is the concentration of compound resulting in 50% inhibition of binding, D is the concentration of radioligand used in the assay, and $K_d$ is the equilibrium dissociation constant for the receptor and the radioligand, determined from saturation binding analysis (shown in Table 1 below).

TABLE 1

$K_d$ Determined from Saturation Binding Analysis.

| $K_d$, nM | | |
|---|---|---|
| hGIPR | hGLP-1R | hGCGR |
| 0.14 | 1.2 | 3.9 |

$K_i$ values of Example compounds and comparators are shown in Table 2.

TABLE 2

In Vitro $K_i$ of Example Compounds and Comparators for hGIPR, hGLP-1R and hGCGR.

| | $K_i$, nM (SEM, n) | | |
|---|---|---|---|
| Compound | hGIPR | hGLP-1R | hGCGR |
| hGIP | 0.186 (0.001,101) | — | — |
| hGLP-1 | — | 0.844 (0.023, 93) | — |
| hGCG | — | — | 3.00 (0.12, 76) |
| Example 1 | 0.111 (0.021, 7) | 4.53 (0.855, 7) | 0.629 (0.0415, 7) |
| Example 2 | 0.158 (0.029, 7) | 2.54 (0.501, 7) | 0.950 (0.350, 7) |
| Example 3 | 0.114 (0.007, 5) | 3.63 (0.386, 5) | 1.73 (0.296, 5) |

NOTE:
A qualifier (>) indicates the data did not reach 50% inhibition relative to maximum binding, whereby the $K_i$ was calculated using the highest concentration tested in the assay. n = 1/x means that only one value out of the total number of replicates (x) is used to express the mean. SEM is only calculated when n = 2 or greater non-qualified results exist.

As seen in Table 2, the Example compounds have binding affinity at each of the hGIPR, hGLP-1R and hGCGR.

Example 5: Functional hGIPR, hGLP-1R and hGCGR Assays

Methods: Functional activity is determined using cAMP formation in HEK-293 clonal cell lines expressing hGIPR, hGLP-1R or hGCGR. hGIPR, hGLP-1R or hGCGR receptor-expressing cells are treated with a control polypeptide or one of Examples 1 to 3 (20 point concentration-response curve in DMSO, 2.75-fold Labcyte Echo direct dilution, 384 well plate Corning Cat #3570) in DMEM (Gibco Cat #31053) supplemented with 1× GlutaMAX™ (Gibco Cat #35050), 0.1% bovine casein (Sigma C4765-10ML), 250 µM IBMX (3-Isobutyl-1-methylxanthine, Acros Cat #228420010) and 20 mM HEPES (Gibco Cat #15630) in a 20 µL assay volume (final DMSO concentration was 0.5%). Experiments also are performed under identical assay conditions with the addition of 1.0% fatty acid free, globulin free human serum albumin (Sigma Cat #A3782).

After a 30-min incubation at 37° C., the resulting increase in intracellular cAMP is quantitatively determined using a CisBio cAMP Dynamic 2 HTRF Assay Kit (62AM4PEJ). Briefly, cAMP levels within the cell are detected by adding the cAMP-d2 conjugate in cell lysis buffer (10 µL) followed by the antibody anti-cAMP-Eu$^{3+}$-Cryptate, also in cell lysis buffer (10 µL). The resulting competitive assay is incubated for at least 60 min at room temperature, and then is detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve. The amount of cAMP generated (nM) in each well is converted to a percent of the maximal response observed with human GIP(1-42)NH$_2$, hGLP-1(7-36)NH$_2$ or hGCG. A relative EC$_{50}$ value and percent top (E$_{max}$) are derived by non-linear regression analysis using the percent maximal response vs. the concentration of peptide added, fitted to a four-parameter logistic equation.

Results: Functional data for hGIP(1-42)NH$_2$, hGLP-1(7-36)NH$_2$, hGCG and the Example compounds are provided below in Table 3 (0.1% bovine casein) and Table 4 (0.1% bovine casein, 1.0% human serum albumin).

TABLE 3

Functional cAMP Potency (EC$_{50}$) and Efficacy (E$_{max}$) for Peptides Incubated at 37° C. (in the presence of 0.1% bovine casein).

| Compound | hGLP-1R [a] | | hGCGR [a] | | hGIPR [a] | |
|---|---|---|---|---|---|---|
| | EC$_{50}$, nM, SEM (n) [b] | E$_{max}$, % ± SEM [c] | EC$_{50}$, nM, SEM (n) [b] | E$_{max}$, % ± SEM [c] | EC$_{50}$, nM, SEM (n) [b] | E$_{max}$, % ± SEM [c] |
| hGLP-1 (7-36)NH$_2$ | 0.395 0.032 (62) | 103 ± 2 | — | — | — | — |
| hGCG | — | — | 2.17 0.17 (63) | 103 ± 2 | — | — |
| hGIP (1-42)NH$_2$ | — | — | — | — | 1.08 0.14 (60) | 98 ± 2 |
| Example 1 | 0.345 0.033 (10) | 106 ± 4 | 1.20 0.12 (10) | 101 ± 3 | 0.0513 0.0099 (10) | 102 ± 2 |
| Example 2 | 0.383 0.089 (10) | 103 ± 3 | 1.02 0.19 (10) | 103 ± 2 | 0.0256 0.0052 (10) | 101 ± 2 |
| Example 3 | 0.451 0.079 (11) | 107 ± 2 | 2.49 0.37 (10) | 99 ± 4 | 0.0306 0.0061 (10) | 103 ± 2 |

NOTE:
[a] Expression density is determined using homologous competition binding of [$^{125}$I]GLP-1(7-36)NH$_2$ at hGLP-1R (112 fmol/mg protein), [$^{125}$I]GCG at hGCGR (98 fmol/mg protein) and [$^{125}$I]GIP(1-42) at hGIPR (124 fmol/mg protein),
[b] EC$_{50}$, nM = the Geometric Mean with the Standard Error of the Mean followed by the number of observations in parenthesis.
[c] E$_{max}$, % = the Arithmetic Mean ± the Standard Error of the Mean for the percent of maximal response to GLP-1(7-36)NH$_2$ at hGLP-1R, GCG at hGCGR or GIP(1-42)NH$_2$ at hGIPR. All values shown are to three (3) significant digits.

TABLE 4

Functional cAMP Potency (EC$_{50}$) and Efficacy (E$_{max}$) for Peptides Incubated at 37° C. (in the presence of 0.1% bovine casein and 1.0% human serum albumin).

| Compound | hGLP-1R [a] | | hGCGR [a] | | hGIPR [a] | |
|---|---|---|---|---|---|---|
| | EC$_{50}$, nM, SEM (n) [b] | E$_{max}$, % ± SEM [c] | EC$_{50}$, nM, SEM (n) [b] | E$_{max}$, % ± SEM [c] | EC$_{50}$, nM, SEM (n) [b] | E$_{max}$, % ± SEM [c] |
| hGLP-1 (7-36)NH$_2$ | 0.368 0.030 (45) | 104 ± 3 | — | — | — | — |
| hGCG | — | — | 2.54 0.30 (45) | 102 ± 3 | — | — |
| hGIP (1-42)NH$_2$ | — | — | — | — | 0.756 0.090 (45) | 96 ± 2 |
| Example 1 | 180 17 (7) | 102 ± 4 | 899 118 (6) | 103 ± 8 | 22.3 5.4 (7) | 100 ± 3 |
| Example 2 | 119 15 (7) | 116 ± 4 | 537 99 (8) | 112 ± 10 | 2.91 0.46 (7) | 99 ± 2 |
| Example 3 | 114 12 (6) | 111 ± 5 | 480 178 (6) | 97 ± 9 | 3.72 0.83 (7) | 105 ± 5 |

NOTE:
[a] Expression density is determined using homologous competition binding of [$^{125}$I]GLP-1(7-36)NH$_2$ at hGLP-1R (112 fmol/mg protein), [$^{125}$I]GCG at hGCGR (98 fmol/mg protein) and [$^{125}$I]GIP(1-42) at hGIPR (124 fmol/mg protein).
[b] EC$_{50}$, nM = the Geometric Mean with the Standard Error of the Mean followed by the number of observations in parenthesis.
[c] E$_{max}$, % = the Arithmetic Mean ± the Standard Error of the Mean for the percent of maximal response to GLP-1(7-36)NH$_2$ at hGLP-1R, GCG at hGCGR or GIP(1-42)NH$_2$ at hGIPR. All values shown are to three (3) significant digits.

As seen in Table 3, Example compounds stimulate cAMP from hGLP-1R, hGCGR and hGIPR in the presence of 0.1% casein.

As seen in Table 4, Example compounds stimulate cAMP from hGLP-1R, hGCGR and hGIPR in the presence of 0.1% bovine casein and 1% human serum albumin.

In Vivo Function

Example 6: Pharmacokinetics in Male Diet-Induced Obese (DIO) Mice

Methods: Male DIO mice are administered a single SQ dose of 200 nmol/kg (0.98 mg/kg) of Example compounds in 40 mM Tris-HCL pH8 buffer with 0.02% PS80 at a volume of 10 mL/kg. Blood is collected at 1, 3, 6, 12, 24, 48 and 72 hr post-dose for pharmacokinetic characterization. Plasma concentration of Example compounds are determined by a qualified Liquid Chromatography Mass Spectrometry (LC/MS) method at Q Squared Solutions BioSciences LLC (Ithaca, NY). The Example compounds and an internal standard are extracted from 100% mouse plasma using protein precipitation followed by solid phase extraction. The intact mass of the Example compounds, which includes peptide plus acyl chain, are detected by a Q-Exactive™ Orbitrap® mass spectrometer.

Results: Data for the Example compounds are provided below in Table 5.

TABLE 5

Mean Plasma Pharmacokinetic Parameters Following
a Single 200 nmol/kg SQ Dose to Male DIO Mice.

| Compound | $t^{1/2}$ (hr) | $T_{max}$ (hr) | $C_{max}$ (nmol/L) | $AUC_{0\text{-}inf}$ (hr*nmol/L) | CL/F (mL/hr/kg) |
|---|---|---|---|---|---|
| Example 1 | 38 | 12 | 817 | 55550 | 3.6 |
| Example 2 | 18 | 12 | 1239 | 42479 | 4.7 |
| Example 3 | 13 | 12 | 1072 | 32800 | 6.1 |

NOTE:

Abbreviations: $t^{1/2}$ = half-life, $T_{max}$ = time to maximum concentration, $C_{max}$ = maximum observed plasma concentration, $AUC_{0\text{-}inf}$ = area under the curve from time 0 hours to infinity, CL/F = clearance/bioavailability.
N = 3 animals/group/time point.

As seen in Table 5, the Example compounds demonstrate an extended pharmacokinetic profile in DIO mice.

Example 7: In Vivo Effect on Insulin Secretion in Male Wistar Rats

Methods: An intravenous glucose tolerance test (ivGTT) in Male Wistar rats is used to estimate insulinotropic potency of the Example compounds. A GLP-1R agonist, semaglutide, is used as a positive control. Rats with surgically implanted cannulas in the jugular vein and carotid artery (Envigo; Indianapolis, IN) 280-320 g are housed one per cage in polycarbonate cages with filter tops. Rats are maintained on a 12-hr light-dark cycle at 21° C. and receive 2014 Teklad Global diet (Envigo) and deionized water ad libitum. Rats are randomized by body weight and dosed 1.5 mL/kg SQ with Example compounds 16 hr prior to glucose administration and then fasted. Stock concentrations of 211 nM/mL of Example compounds are diluted in 40 mM Tris-HCl buffer pH 8.0 with 0.02% PS80 to desired dosing concentrations; doses tested are vehicle, 0.1, 0.3, 1, 3, 10 and 30 nM/kg. Semaglutide is used as positive control in connection with each run of Example compounds (10 nM/kg dose).

A time 0 blood sample is collected into EDTA tubes after which glucose is administered (0.5 mg/kg, 5 mL/kg). Blood samples are collected for glucose and insulin levels at time 2, 4, 6, 10, 20 and 30 min post intravenous administration of glucose. Plasma insulin is determined using an electrochemiluminescence assay (Meso Scale; Rockville, MD). Insulin AUC is examined compared to the vehicle control with n=6 animals per group.

Statistical analysis is performed using JMP with a one-way ANOVA followed by Dunnett's comparison to the vehicle control.

Results: Data for the Example compounds are provided below in Table 6.

TABLE 6

Effect of Vehicle, Semaglutide (Sema at 10 nmol/kg) and Example Compounds on Insulin Secretion During ivGTT in Wistar Rats.

| | $AUC_{30\ min}$ of Insulin After Bolus IV Glucose Dose (nmol/kg) | | | | | | | |
|---|---|---|---|---|---|---|---|---|
| Compound | Vehicle | 0.1 | 0.3 | 1 | 3 | 10 | 30 | Sema |
| Example 1 | 27.8 ± 4.8 | 36.1 ± 5.0 | 45.5 ± 8.4 | 70.4 ± 8.4 | 115.7 ± 6.0 | 145.9 ± 14.9 | 134.5 ± 16.6 | 80.9 ± 8.2 |
| Example 2 | 28.9 ± 7.2 | 69.0 ± 7.4 | 62.6 ± 5.1 | 72.6 ± 4.7 | 101.5 ± 18.2 | 128.8 ± 11.7 | 159.0 ± 14.9 | 76.4 ± 5.6 |
| Example 3 | 37.3 ± 4.1 | 67.0 ± 10.2 | 77.6 ± 6.7 | 86.9 ± 9.1 | 97.2 ± 7.5 | 119.8 ± 10.2 | 174.8 ± 22.1 | 76.6 ± 7.1 |

NOTE:

Results are expressed as Mean ± Standard Error of Means (SEM) of 6 rats per group. The statistical test is one-way ANOVA followed by Dunnett's
*$p < 0.05$ compared to vehicle;
+$p < 0.05$ compared to semaglutide.

As seen in Table 6, the Example compounds dose-dependently increase insulin secretion.

Example 8: In Vivo Studies on Weight Loss, Metabolism and Body Composition in DIO C57/B16 Mice Methods: To investigate the effects of the Example compounds on parameters such as weight loss, metabolism and body composition, the Example compounds are dosed to C57B16 DIO mice. These animals, although not diabetic, display insulin resistance and dyslipidemia, all characteristics of metabolic syndrome, after being placed on a high fat diet for 20 weeks.

Here, DIO male C57/B16 mice at 20 weeks old are maintained on a calorie-rich diet are used in the following studies. Animals are individually housed in a temperature-controlled (23° C. to 26° C.) facility with 12-hr light/dark cycle (lights on 2100) and free access to food (TD95217) and water. After a 3-week acclimation to the facility, which includes 1 week of vehicle acclimation dosing, the mice are randomized according to their body weight, so each experimental group of animals would have similar body weight. The body weights range from 40 g to 51 g.

All groups contain 6 mice. Example compounds and semaglutide are dissolved in vehicle (40 mM Tris-HCl at pH 8.0 with 0.02% PS-80) and are administered by SQ injection (10 mL/kg) to ad libitum-fed DIO mice 30 min to 120 min prior to the onset of the dark cycle every day for 14 days (Days 1 to 14). Body weight and food intake are measured daily throughout the study, including 1 day after last dose (Day 15).

Absolute changes in body weight are calculated by subtracting the body weight of the same animal prior to the first injection of molecule. On Days 0 and 15, total fat mass is measured by nuclear magnetic resonance (NMR) using an Echo Medical System (Houston, TX) instrument. On Day 15, metabolic parameters are measured using Accu-Chek® Aviva® Glucometers (Roche; Indianapolis, IN) or a Hitachi clinical blood analyzer (Roche, Indianapolis, IN). Plasma insulin is determined using an electrochemiluminescence assay (Meso Scale Discovery, Rockville, MD).

Data are presented as mean±SEM of 6 animals per group in Tables 7 and 8 below. Statistical analysis is performed using repeated measures ANOVA, followed by Dunnett's method for multiple comparisons. Significant differences are identified as * with p<0.05.

Results: Data for the Example compounds are provided below in Tables 7 and 8.

TABLE 7

Body Weight Change After Treatment with Semaglutide and Example Compounds After 15 Days.

| Compound | Dose (nmol/kg) | Δ Body Weight (g) | Δ Body Weight (%) | Fat Mass (%) |
|---|---|---|---|---|
| Sema | 10 | −9.23 ± 0.58* | −21.98 ± 2.58* | −15.14 ± 1.93* |
| Example 1 | 0.15625 | −1.20 ± 0.15 | −4.31 ± 0.75 | −2.44 ± 0.63 |
|  | 0.625 | −4.37 ± 0.08* | −11.40 ± 0.92* | −7.38 ± 1.05* |
|  | 2.5 | −10.42 ± 1.40* | −24.43 ± 3.84* | −17.05 ± 2.47* |
|  | 10 | −18.97 ± 0.81* | −43.71 ± 2.32* | −30.07 ± 1.69* |
|  | 20 | −21.30 ± 0.94* | −48.88 ± 2.00* | −32.15 ± 1.93* |
| Example 2 | 0.15625 | −1.72 ± 0.04 | −2.65 ± 0.55 | −1.91 ± 0.84 |
|  | 0.625 | −4.48 ± 0.26* | −8.90 ± 1.38* | −5.87 ± 0.94* |
|  | 2.5 | −8.62 ± 0.21* | −17.90 ± 1.01* | −11.96 ± 0.88* |
|  | 10 | −20.10 ± 0.54* | −43.44 ± 1.30* | −28.53 ± 1.24* |
|  | 20 | −21.77 ± 0.50* | −46.79 ± 1.40* | −28.80 ± 0.81* |
| Example 3 | 0.15625 | −1.95 ± 0.13 | −4.60 ± 0.71 | −3.34 ± 0.60 |
|  | 0.625 | −5.18 ± 0.25* | −11.91 ± 0.99* | −8.03 ± 0.84* |
|  | 2.5 | −11.65 ± 1.68* | −25.98 ± 3.85* | −18.55 ± 2.41* |
|  | 10 | −18.43 ± 0.68* | −41.10 ± 1.51* | −28.50 ± 1.55* |
|  | 20 | −19.92 ± 0.34* | −44.22 ± 1.01* | −29.23 ± 1.29* |

NOTE:
"Δ Body weight (g)" refers to difference between body weight at day 15 between test and vehicle groups. "Δ Body weight (%)" refers to percent decrease in body weight between days 1 and 15 in test groups. "Fat mass (%)" refers to difference between fat mass between days 0 and 15 in test groups. "Sema" means semaglutide. All data is from single representative study. Percent change in body weight and fat mass for animals receiving vehicle is recorded and is less than 2% in each study. The "Δ Body weight (g)", "Δ Body weight (%)", and "Δ Fat mass (%)" and are statistically significantly different (*, p < 0.05) than control for semaglutide and all Examples at all doses tested, except for Example peptides at the low dose, 0.15625 nmol/kg.

As seen in Table 7, the Example compounds dose-dependently reduce body weight and fat mass.

TABLE 8

Effect of Treatment with Example Compounds on Blood Glucose, Insulin, Total Cholesterol and Triglycerides After 15 Days.

| Compound | Dose (nmol/kg) | Δ Glucose (mg/dL) | Δ Insulin (ng/mL) | Δ Cholesterol (mg/dL) | Δ Trigs (mg/dL) |
|---|---|---|---|---|---|
| Sema | 10 | −18.33 ± 2.81 | −4.15 ± 2.23 | −73.33 ± 4.17* | 16.00 ± 0.38 |
| Example 1 | 0.15625 | −18.58 ± 1.04 | −4.48 ± 1.70 | −14.33 ± 4.37 | −27.83 ± 0.44 |
|  | 0.625 | −24.42 ± 4.44* | −6.03 ± 0.94 | −39.17 ± 0.08 | 15.33 ± 2.75 |
|  | 2.5 | −14.67 ± 0.77 | −10.13 ± 4.21 | −118.17 ± 1.57* | −2.83 ± 4.13 |
|  | 10 | −35.08 ± 1.47* | −11.14 ± 4.41* | −164.00 ± 1.85* | −43.00 ± 0.50 |
|  | 20 | −56.00 ± 2.12* | −11.40 ± 4.55* | −179.17 ± 7.73* | −52.50 ± 3.95* |
| Example 2 | 0.15625 | −9.50 ± 5.21 | 14.64 ± 3.28 | −22.00 ± 4.71 | 9.67 ± 7.80 |
|  | 0.625 | −6.17 ± 7.12 | −9.35 ± 5.61 | −43.50 ± 3.47* | −3.50 ± 3.73 |
|  | 2.5 | −13.50 ± 3.92 | −14.01 ± 7.49 | −150.33 ± 1.70* | −2.33 ± 3.07 |
|  | 10 | −41.00 ± 4.18* | −14.52 ± 7.39 | −199.33 ± 7.02* | −9.00 ± 5.09 |
|  | 20 | −46.08 ± 4.21* | −14.73 ± 7.52 | −198.00 ± 5.46* | −15.83 ± 6.63 |
| Example 3 | 0.15625 | −26.97 ± 6.52* | 0.48 ± 1.80 | −14.50 ± 5.03 | 40.67 ± 1.75 |
|  | 0.625 | −19.47 ± 6.65* | −4.49 ± 3.03 | −37.83 ± 4.80* | 40.33 ± 1.58 |
|  | 2.5 | −33.47 ± 1.69* | −7.25 ± 3.60* | −136.50 ± 5.42* | −7.17 ± 6.52 |
|  | 10 | −48.72 ± 6.41* | −7.61 ± 3.80* | −162.50 ± 4.09* | 29.00 ± 21.71 |
|  | 20 | −55.97 ± 6.74* | −7.69 ± 3.79* | −186.83 ± 7.59* | −16.50 ± 1.60 |

NOTE:

All data refers to difference at day 15 between test and vehicle groups and is from a single representative study. "Sema" means semaglutide. *p < 0.05 compared to Vehicle group; one-way ANOVA, Dunnett's.

As seen in Table 8, the Example compounds also reduce blood glucose, insulin (as a sign of increasing insulin sensitivity), cholesterol and triglycerides.

```
                         SEQUENCE LISTING

The following nucleic and/or amino acid sequences are referred to in the
disclosure above and are provided below for reference.
SEQ ID NO: 1 - Human GIP
YAEGTFISDYSIAMDKIHQQDFVNWLLAQKGKKNDWKHNITQ SEQ ID NO: 2 - Human GLP-1₇₋₃₆ amide
HAEGTFTSDVSSYLEGQAAKEFIAWLVKGR-NH₂

SEQ ID NO: 3 - Human glucagon
HSQGTFTSDYSKYLDSRRAQDFVQWLMNT

SEQ ID NO: 4 - Human OXM
HSQGTFTSDYSKYLDSRRAQDFVQWLMNTKRNRNNIA

SEQ ID NO: 5 - Incretin analog
YX₂QGTX₆TSDX₁₀SIX₁₃LDX₁₆X₁₇AQX₂₀X₂₁FIX₂₄X₂₅LLEGGPSSGEPPPX₃₉,
where:
X₂ is Aib,
X₆ is αMeF(2F),
X₁₀ can be Y or 4Pal,
X₁₃ can be L or αMeL,
X₁₆ is Orn,
X₁₇ is any amino acid with a functional group available for conjugation,
X₂₀ can be 4Pal, Iva or αMeL,
X₂₁ can be A or Aib,
X₂₄ can be E or e,
X₂₅ can be Y or αMeY, and
X₃₉ can be E or S SEQ ID NO: 6 - Incretin analog
Y-Aib-QGT-αMeF(2F)-TSDYSILLDOKAQ-4Pal-AFIEYLLEGGPSSGEPPPE SEQ ID NO: 7 - Incretin analog
Y-Aib-QGT-αMeF(2F)-TSDYSI-αMeL-LDOKAQ-Iva-AFIE-αMeY-
LLEGGPSSGEPPPS SEQ ID NO: 8 - Incretin analog
Y-Aib-QGT-αMeF(2F)-TSD-4Pal-SI-αMeL-LDOKAQ-αMeL-Aib-FIe-αaMeY-
LLEGGPSSGEPPPS SEQ ID NO: 9 - Incretin analog
Y-Aib-QGT-αMeF(2F)-TSDYSILLDOK(2-[2-(2-amino-ethoxy)-ethoxy]-acetyl-γE-CO-
(CH₂)₁₈-CO₂H)AQ-4Pal-AFIEYLLEGGPSSGEPPPE-NH₂

SEQ ID NO: 10 - Incretin analog
Y-Aib-QGT-αMeF(2F)-TSDYSI-αMeL-LDOK(2-[2-(2-amino-ethoxy)-ethoxy]-acetyl-
γE-CO-(CH₂)₁₈-CO₂H)AQ-Iva-AFIE-αMeY-LLEGGPSSGEPPPS-NH₂

SEQ ID NO: 11 - Incretin analog
Y-Aib-QGT-αMeF(2F)-TSD-4Pal-SI-αMeL-LDOK(2-[2-(2-amino-ethoxy)-ethoxy]-
acetyl-γE-CO-(CH₂)₁₈-CO₂H)AQ-αMeL-Aib-FIe-αMeY-LLEGGPSSGEPPPS-NH₂

SEQ ID NO: 12 - Artificial sequence
GPSSGEPPPE

SEQ ID NO: 13 - Artificial sequences
GPSSGEPPPS

SEQ ID NO: 14 - human GIP receptor
MTTSPILQLLLRLSLCGLLLQRAETGSKGQTAGELYQRWERYRRECQETLAAAEP
PSGLACNGSFDMYVCWDYAAPNATARASCPWYLPWHHHVAAGFVLRQCGSDG
QWGLWRDHTQCENPEKNEAFLDQRLILERLQVMYTVGYSLSLATLLLALLILSLF
RRLHCTRNYIHINLFTSFMLRAAAILSRDRLLPRPGPYLGDQALALWNQALAACR
TAQIVTQYCVGANYTWLLVEGVYLHSLLVLVGGSEEGHFRYYLLLGWGAPALF
VIPWVIVRYLYENTQCWERNEVKAIWWIIRTPILMTILINFLIFIRILGILLSKLRTRQ
MRCRDYRLRLARSTLTLVPLLGVHEVVFAPVTEEQARGALRFAKLGFEIFLSSFQ
GFLVSVLYCFINKEVQSEIRRGWHHCRLRRSLGEEQRQLPERAFRALPSGSGPGE
VPTSRGLSSGTLPGPGNEASRELESYC SEQ ID NO: 15 - human GLP-1 receptor
MAGAPGPLRLALLLLGMVGRAGPRPQGATVSLWETVQKWREYRRQCQRSLTED
PPPATDLFCNRTFDEYACWPDGEPGSFVNVSCPWYLPWASSVPQGHVYRFCTAE
GLWLQKDNSSLPWRDLSECEESKRGERSSPEEQLLFLYIIYTVGYALSFSALVIAS
AILLGFRHLHCTRNYIHLNLFASFILRALSVFIKDAALKWMYSTAAQQHQWDGLL
```

SEQUENCE LISTING

```
SYQDSLSCRLVFLLMQYCVAANYYWLLVEGVYLYTLLAFSVLSEQWIFRLYVSI
GWGVPLLFVVPWGIVKYLYEDEGCWTRNSNMNYWLIIRLPILFAIGVNFLIFVRVI
CIVVSKLKANLMCKTDIKCRLAKSTLTLIPLLGTHEVIFAFVMDEHARGTLRFIKL
FTELSFTSFQGLMVAILYCFVNNEVQLEFRKSWERWRLEHLHIQRDSSMKPLKCP
TSSLSSGATAGSSMYTATCQASCS

SEQ ID NO: 16 - human GCG receptor
MPPCQPQRPLLLLLLLLACQPQVPSAQVMDFLFEKWKLYGDQCHHNLSLLPPPTL
VCNRTFDKYSCWPDTPANTTANISCPWYLPWHHKVQHRFVFKRCGPDGQWVRG
PRGQPWRDASQCQMDGEEIEVQKEVAKMYSSFQVMYTVGYSLSLGALLLALAIL
GGLSKLHCTRNAIHANLFASFVLKASSVLVIDGLLRTRYSQKIGDDLSVSTWLSD
GAVAGCRVAAVFMQYGIVANYCWLLVEGLYLHNLLGLATLPERSFFSLYLGIG
WGAPMLFVVPWAVVKCLFENVQCWTSNDNMGFWWILRFPVFLAILINFFIFVRI
VQLLVAKLRARQMHHTDYKFRLAKSTLTLIPLLGVHEVVFAFVTDEHAQGTLRS
AKLFFDLFLSSFQGLLVAVLYCFLNKEVQSELRRRWHRWRLGKVLWEERNTSNH
RASSSPGHGPPSKELQFGRGGGSQDSSAETPLAGGLPRLAESPF
```

SEQUENCE LISTING

<160> NUMBER OF SEQ ID NOS: 16

<210> SEQ ID NO 1
<211> LENGTH: 42
<212> TYPE: PRT
<213> ORGANISM: Homo sapiens

<400> SEQUENCE: 1

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 2
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 29
<212> TYPE: PRT
<213> ORGANISM: Homo sapiens

<400> SEQUENCE: 3

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 4
<211> LENGTH: 37
<212> TYPE: PRT

<213> ORGANISM: Homo sapiens

<400> SEQUENCE: 4

His Ser Gln Gly Thr Phe Thr Ser Asp Tyr Ser Lys Tyr Leu Asp Ser
1               5                   10                  15
Arg Arg Ala Gln Asp Phe Val Gln Trp Leu Met Asn Thr Lys Arg Asn
            20                  25                  30
Arg Asn Asn Ile Ala
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (10)..(10)
<223> OTHER INFORMATION: Xaa at position 10 is Y or 4Pal
<220> FEATURE:
<221> NAME/KEY: MISC_FEATURE
<222> LOCATION: (13)..(13)
<223> OTHER INFORMATION: Xaa at position 13 is L or alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (17)..(17)
<223> OTHER INFORMATION: Xaa at position 17 is any amino acid with a
      functional group available for conjugation
<220> FEATURE:
<221> NAME/KEY: MISC_FEATURE
<222> LOCATION: (20)..(20)
<223> OTHER INFORMATION: Xaa at position 20 is 4Pal, Iva, or alpha-MeL
<220> FEATURE:
<221> NAME/KEY: MISC_FEATURE
<222> LOCATION: (21)..(21)
<223> OTHER INFORMATION: Xaa at position 21 is A or Aib
<220> FEATURE:
<221> NAME/KEY: MISC_FEATURE
<222> LOCATION: (24)..(24)
<223> OTHER INFORMATION: Xaa at position 24 is E or D-Glu
<220> FEATURE:
<221> NAME/KEY: MISC_FEATURE
<222> LOCATION: (25)..(25)
<223> OTHER INFORMATION: Xaa at position 25 is Y or alpha-MeY
<220> FEATURE:
<221> NAME/KEY: MISC_FEATURE
<222> LOCATION: (39)..(39)
<223> OTHER INFORMATION: Xaa at position 39 is E or S

<400> SEQUENCE: 5

Tyr Xaa Gln Gly Thr Xaa Thr Ser Asp Xaa Ser Ile Xaa Leu Asp Xaa
1               5                   10                  15
Xaa Ala Gln Xaa Xaa Phe Ile Xaa Xaa Leu Leu Glu Gly Gly Pro Ser
            20                  25                  30
Ser Gly Glu Pro Pro Pro Xaa
        35

<210> SEQ ID NO 6

```
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is 4Pal

<400> SEQUENCE: 6

Tyr Xaa Gln Gly Thr Xaa Thr Ser Asp Tyr Ser Ile Leu Leu Asp Xaa
1               5                   10                  15

Lys Ala Gln Xaa Ala Phe Ile Glu Tyr Leu Leu Glu Gly Gly Pro Ser
            20                  25                  30

Ser Gly Glu Pro Pro Pro Glu
            35

<210> SEQ ID NO 7
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is Iva
<220> FEATURE:
<221> NAME/KEY: MISC_FEATURE
<222> LOCATION: (25)..(25)
<223> OTHER INFORMATION: Xaa at position 25 is alpha-MeY

<400> SEQUENCE: 7

Tyr Xaa Gln Gly Thr Xaa Thr Ser Asp Tyr Ser Ile Xaa Leu Asp Xaa
1               5                   10                  15

Lys Ala Gln Xaa Ala Phe Ile Glu Xaa Leu Leu Glu Gly Gly Pro Ser
            20                  25                  30

Ser Gly Glu Pro Pro Pro Ser
            35

<210> SEQ ID NO 8
<211> LENGTH: 39
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MISC_FEATURE
<222> LOCATION: (20)..(20)
<223> OTHER INFORMATION: Xaa at position 20 is alpha-MeL
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-MeY

<400> SEQUENCE: 8

Tyr Xaa Gln Gly Thr Xaa Thr Ser Asp Xaa Ser Ile Xaa Leu Asp Xaa
1               5                   10                  15

Lys Ala Gln Xaa Xaa Phe Ile Xaa Xaa Leu Leu Glu Gly Gly Pro Ser
            20                  25                  30

Ser Gly Glu Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-Amino-ethoxy)-ethoxy]-acetyl)-(gamma-Glu)-CO-(CH2)18-CO2H
<220> FEATURE:
<221> NAME/KEY: MISC_FEATURE
```

```
<222> LOCATION: (20)..(20)
<223> OTHER INFORMATION: Xaa at position 20 is 4Pal
<220> FEATURE:
<221> NAME/KEY: MOD_RES
<222> LOCATION: (39)..(39)
<223> OTHER INFORMATION: Glutamic acid at position 39 is amidated

<400> SEQUENCE: 9

Tyr Xaa Gln Gly Thr Xaa Thr Ser Asp Tyr Ser Ile Leu Leu Asp Xaa
1               5                   10                  15

Lys Ala Gln Xaa Ala Phe Ile Glu Tyr Leu Leu Glu Gly Gly Pro Ser
            20                  25                  30

Ser Gly Glu Pro Pro Pro Glu
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alpha-MeF(2F)
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-Amino-ethoxy)-ethoxy]-acetyl)-(gamma-Glu)-CO-(CH2)18-CO2H
<220> FEATURE:
<221> NAME/KEY: MISC_FEATURE
<222> LOCATION: (20)..(20)
<223> OTHER INFORMATION: Xaa at position 20 is Iva
<220> FEATURE:
<221> NAME/KEY: MISC_FEATURE
<222> LOCATION: (25)..(25)
<223> OTHER INFORMATION: Xaa at position 25 is alpha-MeY
<220> FEATURE:
<221> NAME/KEY: MOD_RES
<222> LOCATION: (39)..(39)
<223> OTHER INFORMATION: Ser at position 39 is amidated

<400> SEQUENCE: 10

Tyr Xaa Gln Gly Thr Xaa Thr Ser Asp Tyr Ser Ile Xaa Leu Asp Xaa
1               5                   10                  15

Lys Ala Gln Xaa Ala Phe Ile Glu Xaa Leu Leu Glu Gly Gly Pro Ser
            20                  25                  30

Ser Gly Glu Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (2)..(2)
<223> OTHER INFORMATION: Xaa at position 2 is Aib
<220> FEATURE:
<221> NAME/KEY: MISC_FEATURE
<222> LOCATION: (6)..(6)
<223> OTHER INFORMATION: Xaa at position 6 is alphaMeF(2F)
<220> FEATURE:
<221> NAME/KEY: MISC_FEATURE
<222> LOCATION: (10)..(10)
<223> OTHER INFORMATION: Xaa at position 10 is 4Pal
<220> FEATURE:
<221> NAME/KEY: MISC_FEATURE
<222> LOCATION: (13)..(13)
<223> OTHER INFORMATION: Xaa at position 13 is alpha-MeL
<220> FEATURE:
<221> NAME/KEY: MISC_FEATURE
<222> LOCATION: (16)..(16)
<223> OTHER INFORMATION: Xaa at position 16 is Orn
<220> FEATURE:
<221> NAME/KEY: MOD_RES
<222> LOCATION: (17)..(17)
<223> OTHER INFORMATION: K at position 17 is chemically modified by
      conjugation of the epsilon-amino group of the K side chain with
      (2-[2-(2-Amino-ethoxy)-ethoxy]-acetyl)-(gamma-Glu)-CO-(CH2)18-CO2H
<220> FEATURE:
<221> NAME/KEY: MISC_FEATURE
<222> LOCATION: (20)..(20)
<223> OTHER INFORMATION: Xaa at position 20 is alpha-MeL
<220> FEATURE:
<221> NAME/KEY: MISC_FEATURE
<222> LOCATION: (21)..(21)
<223> OTHER INFORMATION: Xaa at position 21 is Aib
<220> FEATURE:
<221> NAME/KEY: MISC_FEATURE
<222> LOCATION: (24)..(24)
<223> OTHER INFORMATION: Xaa at position 24 is D-Glu
<220> FEATURE:
<221> NAME/KEY: MISC_FEATURE
<222> LOCATION: (25)..(25)
<223> OTHER INFORMATION: Xaa at position 25 is alpha-MeY
<220> FEATURE:
<221> NAME/KEY: MISC_FEATURE
<222> LOCATION: (39)..(39)
<223> OTHER INFORMATION: Ser at position 39 is amidated

<400> SEQUENCE: 11

Tyr Xaa Gln Gly Thr Xaa Thr Ser Asp Xaa Ser Ile Xaa Leu Asp Xaa
1               5                   10                  15

Lys Ala Gln Xaa Xaa Phe Ile Xaa Xaa Leu Leu Glu Gly Gly Pro Ser
                20                  25                  30

Ser Gly Glu Pro Pro Pro Ser
        35

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gly Pro Ser Ser Gly Glu Pro Pro Pro Glu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13
```

```
Gly Pro Ser Ser Gly Glu Pro Pro Ser
1               5                   10
```

<210> SEQ ID NO 14
<211> LENGTH: 466
<212> TYPE: PRT
<213> ORGANISM: Homo sapiens

<400> SEQUENCE: 14

```
Met Thr Thr Ser Pro Ile Leu Gln Leu Leu Arg Leu Ser Leu Cys
1               5                   10                  15

Gly Leu Leu Leu Gln Arg Ala Glu Thr Gly Ser Lys Gly Gln Thr Ala
                20                  25                  30

Gly Glu Leu Tyr Gln Arg Trp Glu Arg Tyr Arg Glu Cys Gln Glu
            35                  40                  45

Thr Leu Ala Ala Ala Glu Pro Pro Ser Gly Leu Ala Cys Asn Gly Ser
            50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
                100                 105                 110

Arg Asp His Thr Gln Cys Glu Asn Pro Glu Lys Asn Glu Ala Phe Leu
                115                 120                 125

Asp Gln Arg Leu Ile Leu Glu Arg Leu Gln Val Met Tyr Thr Val Gly
            130                 135                 140

Tyr Ser Leu Ser Leu Ala Thr Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
                180                 185                 190

Leu Leu Pro Arg Pro Gly Pro Tyr Leu Gly Asp Gln Ala Leu Ala Leu
            195                 200                 205

Trp Asn Gln Ala Leu Ala Ala Cys Arg Thr Ala Gln Ile Val Thr Gln
        210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
                260                 265                 270

Pro Trp Val Ile Val Arg Tyr Leu Tyr Glu Asn Thr Gln Cys Trp Glu
            275                 280                 285

Arg Asn Glu Val Lys Ala Ile Trp Trp Ile Ile Arg Thr Pro Ile Leu
            290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
                340                 345                 350

His Glu Val Val Phe Ala Pro Val Thr Glu Glu Gln Ala Arg Gly Ala
```

```
                355                 360                 365
Leu Arg Phe Ala Lys Leu Gly Phe Glu Ile Phe Leu Ser Ser Phe Gln
370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
                420                 425                 430

Ser Gly Ser Gly Pro Gly Glu Val Pro Thr Ser Arg Gly Leu Ser Ser
                435                 440                 445

Gly Thr Leu Pro Gly Pro Gly Asn Glu Ala Ser Arg Glu Leu Glu Ser
450                 455                 460

Tyr Cys
465

<210> SEQ ID NO 15
<211> LENGTH: 463
<212> TYPE: PRT
<213> ORGANISM: Homo sapiens

<400> SEQUENCE: 15

Met Ala Gly Ala Pro Gly Pro Leu Arg Leu Ala Leu Leu Leu Leu Gly
1               5                   10                  15

Met Val Gly Arg Ala Gly Pro Arg Pro Gln Gly Ala Thr Val Ser Leu
                20                  25                  30

Trp Glu Thr Val Gln Lys Trp Arg Glu Tyr Arg Arg Gln Cys Gln Arg
            35                  40                  45

Ser Leu Thr Glu Asp Pro Pro Ala Thr Asp Leu Phe Cys Asn Arg
        50                  55                  60

Thr Phe Asp Glu Tyr Ala Cys Trp Pro Asp Gly Glu Pro Gly Ser Phe
65                  70                  75                  80

Val Asn Val Ser Cys Pro Trp Tyr Leu Pro Trp Ala Ser Ser Val Pro
                85                  90                  95

Gln Gly His Val Tyr Arg Phe Cys Thr Ala Glu Gly Leu Trp Leu Gln
            100                 105                 110

Lys Asp Asn Ser Ser Leu Pro Trp Arg Asp Leu Ser Glu Cys Glu Glu
        115                 120                 125

Ser Lys Arg Gly Glu Arg Ser Ser Pro Glu Glu Gln Leu Leu Phe Leu
    130                 135                 140

Tyr Ile Ile Tyr Thr Val Gly Tyr Ala Leu Ser Phe Ser Ala Leu Val
145                 150                 155                 160

Ile Ala Ser Ala Ile Leu Leu Gly Phe Arg His Leu His Cys Thr Arg
                165                 170                 175

Asn Tyr Ile His Leu Asn Leu Phe Ala Ser Phe Ile Leu Arg Ala Leu
            180                 185                 190

Ser Val Phe Ile Lys Asp Ala Ala Leu Lys Trp Met Tyr Ser Thr Ala
        195                 200                 205

Ala Gln Gln His Gln Trp Asp Gly Leu Leu Ser Tyr Gln Asp Ser Leu
    210                 215                 220

Ser Cys Arg Leu Val Phe Leu Leu Met Gln Tyr Cys Val Ala Ala Asn
225                 230                 235                 240

Tyr Tyr Trp Leu Leu Val Glu Gly Val Tyr Leu Tyr Thr Leu Leu Ala
                245                 250                 255
```

```
Phe Ser Val Leu Ser Glu Gln Trp Ile Phe Arg Leu Tyr Val Ser Ile
                260                 265                 270

Gly Trp Gly Val Pro Leu Leu Phe Val Pro Trp Gly Ile Val Lys
            275                 280                 285

Tyr Leu Tyr Glu Asp Glu Gly Cys Trp Thr Arg Asn Ser Asn Met Asn
            290                 295                 300

Tyr Trp Leu Ile Ile Arg Leu Pro Ile Leu Phe Ala Ile Gly Val Asn
305                 310                 315                 320

Phe Leu Ile Phe Val Arg Val Ile Cys Ile Val Ser Lys Leu Lys
                325                 330                 335

Ala Asn Leu Met Cys Lys Thr Asp Ile Lys Cys Arg Leu Ala Lys Ser
            340                 345                 350

Thr Leu Thr Leu Ile Pro Leu Leu Gly Thr His Glu Val Ile Phe Ala
            355                 360                 365

Phe Val Met Asp Glu His Ala Arg Gly Thr Leu Arg Phe Ile Lys Leu
            370                 375                 380

Phe Thr Glu Leu Ser Phe Thr Ser Phe Gln Gly Leu Met Val Ala Ile
385                 390                 395                 400

Leu Tyr Cys Phe Val Asn Asn Glu Val Gln Leu Glu Phe Arg Lys Ser
                405                 410                 415

Trp Glu Arg Trp Arg Leu Glu His Leu His Ile Gln Arg Asp Ser Ser
            420                 425                 430

Met Lys Pro Leu Lys Cys Pro Thr Ser Ser Leu Ser Ser Gly Ala Thr
            435                 440                 445

Ala Gly Ser Ser Met Tyr Thr Ala Thr Cys Gln Ala Ser Cys Ser
450                 455                 460

<210> SEQ ID NO 16
<211> LENGTH: 476
<212> TYPE: PRT
<213> ORGANISM: Homo sapiens

<400> SEQUENCE: 16

Met Pro Pro Cys Gln Pro Gln Arg Pro Leu Leu Leu Leu Leu Leu Leu
1               5                   10                  15

Leu Ala Cys Gln Pro Gln Val Pro Ser Ala Gln Val Met Asp Phe Leu
            20                  25                  30

Phe Glu Lys Trp Lys Leu Tyr Gly Asp Gln Cys His His Asn Leu Ser
            35                  40                  45

Leu Leu Pro Pro Pro Thr Leu Val Cys Asn Arg Thr Phe Asp Lys Tyr
        50                  55                  60

Ser Cys Trp Pro Asp Thr Pro Ala Asn Thr Thr Ala Asn Ile Ser Cys
65                  70                  75                  80

Pro Trp Tyr Leu Pro Trp His His Lys Val Gln His Arg Phe Val Phe
                85                  90                  95

Lys Arg Cys Gly Pro Asp Gly Gln Trp Val Arg Gly Pro Arg Gly Gln
            100                 105                 110

Pro Trp Arg Asp Ala Ser Gln Cys Gln Met Asp Gly Glu Glu Ile Glu
            115                 120                 125

Val Gln Lys Glu Val Ala Lys Met Tyr Ser Ser Phe Gln Val Met Tyr
130                 135                 140

Thr Val Gly Tyr Ser Leu Ser Leu Gly Ala Leu Leu Leu Ala Leu Ala
145                 150                 155                 160

Ile Leu Gly Gly Leu Ser Lys Leu His Cys Thr Arg Asn Ala Ile His
                165                 170                 175
```

```
Ala Asn Leu Phe Ala Ser Phe Val Leu Lys Ala Ser Ser Val Leu Val
            180             185             190

Ile Asp Gly Leu Leu Arg Thr Arg Tyr Ser Gln Lys Ile Gly Asp Asp
        195             200             205

Leu Ser Val Ser Thr Trp Leu Ser Asp Gly Ala Val Ala Gly Cys Arg
    210             215             220

Val Ala Ala Val Phe Met Gln Tyr Gly Ile Val Ala Asn Tyr Cys Trp
225             230             235             240

Leu Leu Val Glu Gly Leu Tyr Leu His Asn Leu Leu Gly Leu Ala Thr
            245             250             255

Leu Pro Glu Arg Ser Phe Phe Ser Leu Tyr Leu Gly Ile Gly Trp Gly
            260             265             270

Ala Pro Met Leu Phe Val Val Pro Trp Ala Val Val Lys Cys Leu Phe
            275             280             285

Glu Asn Val Gln Cys Trp Thr Ser Asn Asp Asn Met Gly Phe Trp Trp
        290             295             300

Ile Leu Arg Phe Pro Val Phe Leu Ala Ile Leu Ile Asn Phe Phe Ile
305             310             315             320

Phe Val Arg Ile Val Gln Leu Leu Val Ala Lys Leu Arg Ala Arg Gln
                325             330             335

Met His His Thr Asp Tyr Lys Phe Arg Leu Ala Lys Ser Thr Leu Thr
            340             345             350

Leu Ile Pro Leu Leu Gly Val His Glu Val Val Phe Ala Phe Val Thr
            355             360             365

Asp Glu His Ala Gln Gly Thr Leu Arg Ser Ala Lys Leu Phe Phe Asp
        370             375             380

Leu Phe Leu Ser Ser Phe Gln Gly Leu Leu Val Ala Val Leu Tyr Cys
385             390             395             400

Phe Leu Asn Lys Glu Val Gln Ser Glu Leu Arg Arg Arg Trp His Arg
            405             410             415

Trp Arg Leu Gly Lys Val Leu Trp Glu Glu Arg Asn Thr Ser Asn His
            420             425             430

Arg Ala Ser Ser Ser Pro Gly His Gly Pro Pro Ser Lys Glu Leu Gln
            435             440             445

Phe Gly Arg Gly Gly Gly Ser Gln Asp Ser Ser Ala Glu Thr Pro Leu
    450             455             460

Ala Gly Gly Leu Pro Arg Leu Ala Glu Ser Pro Phe
465             470             475
```

The invention claimed is:

1. A compound comprising:

(SEQ ID NO: 5)
YX$_2$QGTX$_6$TSDX$_{10}$SIX$_{13}$LDX$_{16}$X$_{17}$AQX$_{20}$X$_{21}$FIX$_{24}$X$_{25}$LLEGGPSSGEPPX$_{39}$, wherein X$_2$ is Aib,
X$_6$ is αMeF(2F),
X$_{10}$ can be Y or 4Pal,
X$_{13}$ can be L or αMeL,
X$_{16}$ is Orn,
X$_{17}$ is any amino acid with a functional group available for conjugation and the functional group is conjugated to a C$_{16}$-C$_{22}$ fatty acid moiety,
X$_{20}$ can be 4Pal, Iva or αMeL,
X$_{21}$ can be A or Aib,
X$_{24}$ can be E or e,
X$_{25}$ can be Y or αMeY, and
X$_{39}$ can be E or S, and
wherein a carboxy-terminal (C-terminal) amino acid optionally is amidated;
or a pharmaceutically acceptable salt thereof.

2. The compound of claim 1, wherein the amino acid with a functional group available for conjugation at position X$_{17}$ is selected from the group consisting of C, D, E, K and Q.

3. The compound of claim 1, wherein the amino acid with a functional group available for conjugation at position X$_{17}$ is K.

4. The compound of claim 1, wherein the amino acid with the functional group available for conjugation at position X$_{17}$ and the C$_{16}$-C$_{22}$ fatty acid moiety are conjugated by a linker between the amino acid and the fatty acid moiety.

5. The compound of claim 4, wherein the linker comprises one to four amino acids.

6. The compound of claim 5, wherein the amino acids are E or γE.

7. The compound of claim 4, wherein the linker further comprises the following structure:

H—{NH—CH$_2$—CH$_2$—[O—CH$_2$—CH$_2$]$_m$—O—(CH$_2$)$_p$—CO}$_n$—OH, wherein m is any integer from 1 to 12, n is any integer from 1 to 12, and p is 1 or 2.

8. The compound of claim 4, wherein the linker further comprises one to four (2-[2-(2-amino-ethoxy)-ethoxy]-acetyl) moieties.

9. The compound of claim 1, wherein $X_{17}$ is K chemically modified through conjugation to an epsilon-amino group of a K side-chain with the following structure:

(2-[2-(2-amino-ethoxy)-ethoxy]-acetyl)$_a$-(γE)$_b$—CO—(CH$_2$)$_c$—CO$_2$H, wherein a is 0, 1 or 2; b is 1 or 2; and c is an integer between 16 to 20.

10. The compound of claim 9, wherein a is 1.
11. The compound of claim 9, wherein a is 2.
12. The compound of claim 9, wherein b is 1.
13. The compound of claim 9, wherein b is 2.
14. The compound of claim 9, wherein c is 20.
15. The compound of claim 1, wherein $X_{10}$ is Y.
16. The compound of claim 1, wherein $X_{10}$ is 4Pal.
17. The compound of claim 1, wherein $X_{13}$ is L.
18. The compound of claim 1, wherein $X_{13}$ is αMeL.
19. The compound of claim 1, wherein $X_{20}$ is 4Pal.
20. The compound of claim 1, wherein $X_{20}$ is Iva.
21. The compound of claim 1, wherein $X_{20}$ is αMeL.
22. The compound of claim 1, wherein $X_{21}$ is A.
23. The compound of claim 1, wherein $X_{21}$ is Aib.
24. The compound of claim 1, wherein $X_{24}$ is E.
25. The compound of claim 1, wherein $X_{24}$ is e.
26. The compound of claim 1, wherein $X_{25}$ is Y.
27. The compound of claim 1, wherein $X_{25}$ is αMeY.
28. The compound of claim 1, wherein $X_{39}$ is E.
29. The compound of claim 1, wherein $X_{39}$ is S.

30. A compound having a formula selected from the group consisting of SEQ ID NOS: 6-11, or a pharmaceutically acceptable salt thereof.

31. A method of treating a disease selected from the group consisting of type 2 diabetes mellitus, dyslipidemia, metabolic syndrome, non-alcoholic fatty liver disease, non-alcoholic steatohepatitis and obesity, the method comprising the step of:
administering to an individual in need thereof an effective amount of a compound of claim 1.

32. A method of treating type 2 diabetes mellitus, the method comprising the step of:
administering to an individual in need thereof an effective amount of compound of claim 1.

33. A pharmaceutical composition comprising:
compound of claim 1; and
a pharmaceutically acceptable carrier, diluent, or excipient.

* * * * *

UNITED STATES PATENT AND TRADEMARK OFFICE
CERTIFICATE OF CORRECTION

Page 1 of 1

PATENT NO. : 12,410,227 B2
APPLICATION NO. : 17/785758
DATED : September 9, 2025
INVENTOR(S) : Milata Mary Abraham et al.

It is certified that error appears in the above-identified patent and that said Letters Patent is hereby corrected as shown below:

On the Title Page

Column 1, at item (71), delete "Lily" and insert --Lilly--.

In the Claims

In Column 53, Claim 1, Lines 56 and 57, delete "SGEPP PX39" and, at the end of the remaining sequence on Line 56, insert --SGEPPPX39,--.

Signed and Sealed this
Tenth Day of February, 2026

John A. Squires
*Director of the United States Patent and Trademark Office*